(12) United States Patent
Altarac et al.

(10) Patent No.: US 11,071,629 B2
(45) Date of Patent: Jul. 27, 2021

(54) INTERBODY SPACER

(71) Applicant: Neurostructures, Inc., Irvine, CA (US)

(72) Inventors: Moti Altarac, Irvine, CA (US); Joey Reglos, Irvine, CA (US); Alan Goodin, Las Vegas, NV (US)

(73) Assignee: NeuroStructures Inc., Irvine, CA (US)

( * ) Notice: Subject to any disclaimer, the term of this patent is extended or adjusted under 35 U.S.C. 154(b) by 197 days.

(21) Appl. No.: 16/159,610

(22) Filed: Oct. 13, 2018

(65) Prior Publication Data

US 2020/0113699 A1 Apr. 16, 2020

(51) Int. Cl.
*A61F 2/44* (2006.01)
*A61F 2/30* (2006.01)

(52) U.S. Cl.
CPC ...... *A61F 2/30749* (2013.01); *A61F 2/30771* (2013.01); *A61F 2/4455* (2013.01); *A61F 2002/3082* (2013.01); *A61F 2002/30082* (2013.01); *A61F 2002/30495* (2013.01); *A61F 2002/30507* (2013.01); *A61F 2002/30517* (2013.01); *A61F 2002/30784* (2013.01)

(58) Field of Classification Search
CPC ........... A61F 2/30749; A61F 2/4455; A61F 2002/30082; A61F 2002/30495; A61F 2002/30507; A61F 2002/30517; A61F 2002/30784; A61F 2002/3082
USPC ............................. 623/17.11–17.16
See application file for complete search history.

(56) References Cited

U.S. PATENT DOCUMENTS

| | | |
|---|---|---|
| 3,741,205 A | 6/1973 | Markoff et al. |
| 5,085,660 A | 2/1992 | Lin |
| 5,364,399 A | 11/1994 | Lowery et al. |
| 5,423,826 A | 6/1995 | Coates et al. |
| 5,549,612 A | 8/1996 | Yapp et al. |
| 5,616,142 A | 4/1997 | Yuan et al. |
| 5,616,144 A | 4/1997 | Yapp et al. |
| 6,045,552 A | 4/2000 | Zucherman et al. |
| 6,139,550 A | 10/2000 | Michelson |
| 6,398,783 B1 | 6/2002 | Michelson |
| 6,527,776 B1 | 3/2003 | Michelson |

(Continued)

FOREIGN PATENT DOCUMENTS

| | | |
|---|---|---|
| EP | 1520545 B1 | 11/2006 |
| EP | 1429675 B1 | 10/2007 |

(Continued)

*Primary Examiner* — Jessica Weiss
(74) *Attorney, Agent, or Firm* — Rimas Lukas

(57) ABSTRACT

An interbody spacer for the spine is provided. The interbody spacer includes a cage and bone screws configured to anchor the cage between two vertebrae of the spine. The cage includes a screw plate configured to mate with the cage in a front-loading fashion. The screw plate is interchangeable with another screw plate configured to receive a different number of bone screws. For example, one screw plate adapted for three bone screws is interchangeable with another screw plate adapted for four bone screws and removably connected to the same cage. The screw plate is connectable intraoperatively or pre-assembled. Each screw plate is also provided with an anti-backout mechanism to retain the bone screws and prevent the bone screws from backing out with respect to the screw plate. The anti-backout mechanism includes a cover plate, locking screw or retaining ring.

10 Claims, 21 Drawing Sheets

(56) References Cited

U.S. PATENT DOCUMENTS

| | | |
|---|---|---|
| 6,599,290 B2 | 7/2003 | Bailey et al. |
| 6,602,255 B1 | 8/2003 | Campbell et al. |
| 6,626,907 B2 | 9/2003 | Campbell et al. |
| 6,652,525 B1 | 11/2003 | Assaker et al. |
| 6,695,846 B2 | 2/2004 | Richelsoph et al. |
| 6,926,718 B1 | 8/2005 | Michelson |
| 6,936,051 B2 | 8/2005 | Michelson |
| 6,964,664 B2 | 11/2005 | Fried et al. |
| 7,175,623 B2 | 2/2007 | Thramann et al. |
| 7,186,254 B2 | 3/2007 | Dinh et al. |
| 7,220,263 B2 | 5/2007 | Cordaro |
| 7,273,481 B2 | 9/2007 | Lombardo et al. |
| 7,276,070 B2 | 10/2007 | Muckter |
| 7,278,997 B1 | 10/2007 | Mueller et al. |
| 7,288,094 B2 | 10/2007 | Lindemann et al. |
| 7,288,095 B2 | 10/2007 | Baynham et al. |
| 7,291,152 B2 | 11/2007 | Abdou |
| 7,306,605 B2 | 12/2007 | Ross |
| 7,318,825 B2 | 1/2008 | Butler et al. |
| 7,524,325 B2 | 4/2009 | Khalili |
| 7,601,170 B2 | 10/2009 | Winslow et al. |
| 7,651,517 B2 | 1/2010 | Konieczynski et al. |
| 7,662,154 B2 | 2/2010 | Ribeiro |
| 7,686,806 B2 | 3/2010 | Rhyne |
| 7,704,255 B2 | 4/2010 | Michelson |
| 7,740,630 B2 | 6/2010 | Michelson |
| 7,803,157 B2 | 9/2010 | Michelson |
| 7,811,285 B2 | 10/2010 | Michelson |
| 7,815,666 B2 | 10/2010 | Baynham et al. |
| 7,824,432 B2 | 11/2010 | Michelson |
| 7,887,547 B2 | 2/2011 | Campbell et al. |
| 8,048,075 B2 | 11/2011 | Michelson |
| 8,206,293 B2 | 6/2012 | Reglos et al. |
| 8,439,924 B1 | 5/2013 | McBride et al. |
| 8,460,308 B2 | 6/2013 | Marino et al. |
| 8,652,182 B1 | 2/2014 | Walker et al. |
| 8,668,723 B2 | 3/2014 | Altarac et al. |
| 9,743,958 B2 | 8/2017 | Ishii et al. |
| 10,016,224 B2 | 7/2018 | Altarac et al. |
| 2002/0120270 A1 | 8/2002 | Trieu et al. |
| 2003/0060828 A1 | 3/2003 | Michelson |
| 2003/0093082 A1 | 5/2003 | Campbell et al. |
| 2003/0105462 A1 | 6/2003 | Haider |
| 2003/0105466 A1 | 6/2003 | Ralph et al. |
| 2003/0105467 A1 | 6/2003 | Ralph et al. |
| 2003/0125739 A1 | 7/2003 | Bagga et al. |
| 2003/0135216 A1 | 7/2003 | Sevrain |
| 2003/0153920 A1 | 8/2003 | Ralph et al. |
| 2003/0171753 A1 | 9/2003 | Collins et al. |
| 2003/0181912 A1 | 9/2003 | Michelson |
| 2003/0187440 A1 | 10/2003 | Richelsoph et al. |
| 2003/0187442 A1 | 10/2003 | Richelsoph et al. |
| 2003/0187509 A1 | 10/2003 | Lemole, Jr. |
| 2003/0191471 A1 | 10/2003 | Michelson |
| 2003/0191472 A1 | 10/2003 | Michelson |
| 2003/0208204 A1 | 11/2003 | Bailey et al. |
| 2003/0229348 A1 | 12/2003 | Sevrain |
| 2003/0236528 A1 | 12/2003 | Thramann |
| 2004/0006343 A1 | 1/2004 | Sevrain |
| 2004/0015169 A1 | 1/2004 | Gause |
| 2004/0019353 A1 | 1/2004 | Freid et al. |
| 2004/0024081 A1 | 2/2004 | Trieu et al. |
| 2004/0030336 A1 | 2/2004 | Khanna |
| 2004/0034352 A1 | 2/2004 | Needham et al. |
| 2004/0039387 A1 | 2/2004 | Gause et al. |
| 2004/0049279 A1 | 3/2004 | Sevrain |
| 2004/0068319 A1 | 4/2004 | Cordaro |
| 2004/0087945 A1 | 5/2004 | Ralph et al. |
| 2004/0087951 A1 | 5/2004 | Khalili |
| 2004/0092929 A1 | 5/2004 | Zindrick |
| 2004/0092947 A1 | 5/2004 | Foley |
| 2004/0097925 A1 | 5/2004 | Boehm, Jr. et al. |
| 2004/0097934 A1 | 5/2004 | Farris et al. |
| 2004/0097935 A1 | 5/2004 | Richelsoph et al. |
| 2004/0097938 A1 | 5/2004 | Alleyne |
| 2004/0097950 A1 | 5/2004 | Foley et al. |
| 2004/0106924 A1 | 6/2004 | Ralph et al. |
| 2004/0122426 A1 | 6/2004 | Michelson |
| 2004/0127897 A1 | 7/2004 | Freid et al. |
| 2004/0127899 A1 | 7/2004 | Konieczynski et al. |
| 2004/0127900 A1 | 7/2004 | Konieczynski et al. |
| 2004/0133205 A1 | 7/2004 | Thramann et al. |
| 2004/0153088 A1 | 8/2004 | Ralph et al. |
| 2004/0158246 A1 | 8/2004 | Assaker et al. |
| 2004/0177847 A1 | 9/2004 | Foley et al. |
| 2004/0181226 A1 | 9/2004 | Michelson |
| 2004/0181229 A1 | 9/2004 | Michelson |
| 2004/0186476 A1 | 9/2004 | Michelson |
| 2004/0204710 A1 | 10/2004 | Patel et al. |
| 2004/0204712 A1 | 10/2004 | Kolb et al. |
| 2004/0204713 A1 | 10/2004 | Abdou |
| 2004/0210314 A1 | 10/2004 | Michelson |
| 2004/0215192 A1 | 10/2004 | Justis et al. |
| 2004/0215195 A1 | 10/2004 | Shipp et al. |
| 2004/0220571 A1 | 11/2004 | Assaker et al. |
| 2004/0220572 A1 | 11/2004 | Michelson |
| 2004/0225290 A1 | 11/2004 | Ferree |
| 2004/0236333 A1 | 11/2004 | Lin |
| 2004/0236334 A1 | 11/2004 | Michelson |
| 2004/0236335 A1 | 11/2004 | Michelson |
| 2004/0243128 A1 | 12/2004 | Howland |
| 2004/0260306 A1 | 12/2004 | Fallin et al. |
| 2005/0015092 A1 | 1/2005 | Rathbun et al. |
| 2005/0015093 A1 | 1/2005 | Suh et al. |
| 2005/0027296 A1 | 2/2005 | Thramann et al. |
| 2005/0027297 A1 | 2/2005 | Michelson |
| 2005/0027298 A1 | 2/2005 | Michelson |
| 2005/0033298 A1 | 2/2005 | Hawkes et al. |
| 2005/0038436 A1 | 2/2005 | Michelson |
| 2005/0043732 A1 | 2/2005 | Dalton |
| 2005/0059970 A1 | 3/2005 | Kolb |
| 2005/0059971 A1 | 3/2005 | Michelson |
| 2005/0075633 A1 | 4/2005 | Ross |
| 2005/0085816 A1 | 4/2005 | Michelson |
| 2005/0137597 A1 | 6/2005 | Butler et al. |
| 2005/0149021 A1 | 7/2005 | Tozzi |
| 2005/0149026 A1 | 7/2005 | Butler et al. |
| 2005/0149027 A1 | 7/2005 | Campbell et al. |
| 2005/0171551 A1 | 8/2005 | Sukovich et al. |
| 2005/0177160 A1 | 8/2005 | Baynham et al. |
| 2005/0177161 A1 | 8/2005 | Baynham et al. |
| 2005/0177163 A1 | 8/2005 | Abdou |
| 2005/0187552 A1 | 8/2005 | Michelson |
| 2005/0187553 A1 | 8/2005 | Grabowski et al. |
| 2005/0187554 A1 | 8/2005 | Michelson |
| 2005/0192576 A1 | 9/2005 | Michelson |
| 2005/0208095 A1 | 9/2005 | Hunter et al. |
| 2005/0209593 A1 | 9/2005 | Kolb |
| 2005/0216005 A1 | 9/2005 | Howland |
| 2005/0216009 A1 | 9/2005 | Michelson |
| 2005/0216010 A1 | 9/2005 | Michelson |
| 2005/0228386 A1 | 10/2005 | Ziolo et al. |
| 2005/0234455 A1 | 10/2005 | Binder et al. |
| 2005/0261690 A1 | 11/2005 | Binder et al. |
| 2005/0273105 A1 | 12/2005 | Konieczynski et al. |
| 2005/0277930 A1 | 12/2005 | Parsons |
| 2005/0277938 A1 | 12/2005 | Parsons |
| 2006/0009845 A1 | 1/2006 | Chin |
| 2006/0030852 A1 | 2/2006 | Sevrain |
| 2006/0079961 A1 | 4/2006 | Michelson |
| 2006/0082015 A1 | 4/2006 | Happonen et al. |
| 2006/0085001 A1 | 4/2006 | Michelson |
| 2006/0149251 A1 | 7/2006 | Ziolo et al. |
| 2006/0149256 A1 | 7/2006 | Wagner et al. |
| 2006/0155298 A1 | 7/2006 | Mueller et al. |
| 2006/0161157 A1 | 7/2006 | Mosca et al. |
| 2006/0167456 A1 | 7/2006 | Johnston et al. |
| 2006/0189997 A1 | 8/2006 | Guenther et al. |
| 2006/0200134 A1 | 9/2006 | Freid et al. |
| 2006/0200146 A1 | 9/2006 | Doubler et al. |
| 2006/0200147 A1 | 9/2006 | Ensign et al. |
| 2006/0229620 A1 | 10/2006 | Rothman et al. |
| 2006/0235405 A1 | 10/2006 | Hawkes |
| 2006/0241611 A1 | 10/2006 | Castro |

(56) References Cited

U.S. PATENT DOCUMENTS

| | | | |
|---|---|---|---|
| 2006/0241616 A1 | 10/2006 | Konieczynski et al. | |
| 2006/0276792 A1 | 12/2006 | Ensign et al. | |
| 2006/0287653 A1 | 12/2006 | Rhyne | |
| 2007/0083203 A1 | 4/2007 | Ribeiro | |
| 2007/0123884 A1 | 5/2007 | Abdou | |
| 2007/0167954 A1 | 7/2007 | Sicvol et al. | |
| 2007/0185489 A1 | 8/2007 | Abdou | |
| 2007/0203492 A1 | 8/2007 | Needham et al. | |
| 2007/0213728 A1 | 9/2007 | Lindemann et al. | |
| 2007/0213729 A1 | 9/2007 | Lindemann et al. | |
| 2007/0213820 A1 | 9/2007 | Magerl et al. | |
| 2007/0213828 A1 | 9/2007 | Trieu et al. | |
| 2007/0225707 A1 | 9/2007 | Wisnewski et al. | |
| 2007/0225717 A1 | 9/2007 | Hawkes | |
| 2007/0225718 A1 | 9/2007 | Ensign | |
| 2007/0233070 A1 | 10/2007 | Young | |
| 2007/0233072 A1 | 10/2007 | Dickinson et al. | |
| 2007/0233107 A1 | 10/2007 | Zielinski | |
| 2007/0233108 A1 | 10/2007 | Stalcup et al. | |
| 2007/0233110 A1 | 10/2007 | Muhanna et al. | |
| 2007/0233117 A1 | 10/2007 | Butler et al. | |
| 2007/0233118 A1 | 10/2007 | McLain | |
| 2007/0233119 A1 | 10/2007 | Markworth | |
| 2007/0233120 A1 | 10/2007 | Thramann et al. | |
| 2007/0239158 A1 | 10/2007 | Trieu et al. | |
| 2007/0270851 A1 | 11/2007 | Erickson et al. | |
| 2007/0270965 A1 | 11/2007 | Ferguson | |
| 2007/0276371 A1 | 11/2007 | Baynham et al. | |
| 2007/0276405 A1 | 11/2007 | Huebner et al. | |
| 2008/0021470 A1 | 1/2008 | Ross | |
| 2008/0051794 A1 | 2/2008 | Dec et al. | |
| 2008/0208260 A1 | 8/2008 | Truckai et al. | |
| 2008/0208262 A1 | 8/2008 | Butler et al. | |
| 2008/0208263 A1 | 8/2008 | Butler et al. | |
| 2008/0208341 A1 | 8/2008 | McCormack et al. | |
| 2008/0215097 A1 | 9/2008 | Ensign et al. | |
| 2008/0228226 A1 | 9/2008 | Shamie | |
| 2008/0228230 A1 | 9/2008 | Ferree | |
| 2008/0234680 A1 | 9/2008 | Zaiser et al. | |
| 2008/0234681 A1 | 9/2008 | Baynham | |
| 2008/0234689 A1 | 9/2008 | Melkent et al. | |
| 2008/0234748 A1 | 9/2008 | Wallenstein et al. | |
| 2008/0234749 A1 | 9/2008 | Forstein | |
| 2008/0234750 A1 | 9/2008 | Woods et al. | |
| 2008/0234751 A1 | 9/2008 | McClintock | |
| 2008/0234752 A1 | 9/2008 | Dahners | |
| 2008/0234753 A1 | 9/2008 | Trieu | |
| 2008/0234755 A1 | 9/2008 | Henderson et al. | |
| 2008/0269806 A1 | 10/2008 | Zhang et al. | |
| 2008/0287999 A1 | 11/2008 | Markworth | |
| 2008/0288001 A1 | 11/2008 | Cawley et al. | |
| 2009/0105831 A1* | 4/2009 | Jones | A61B 17/8042 623/17.16 |
| 2009/0131988 A1 | 5/2009 | Bush, Jr. et al. | |
| 2009/0149888 A1 | 6/2009 | Abdelgany | |
| 2009/0171397 A1 | 7/2009 | Rothman et al. | |
| 2009/0177237 A1 | 7/2009 | Zucherman et al. | |
| 2009/0177239 A1 | 7/2009 | Castro | |
| 2009/0182341 A1 | 7/2009 | Link et al. | |
| 2009/0182383 A1 | 7/2009 | Prybyla et al. | |
| 2009/0187218 A1 | 7/2009 | Schaffhausen | |
| 2009/0192549 A1 | 7/2009 | Sanders et al. | |
| 2009/0210008 A1 | 8/2009 | Butler et al. | |
| 2009/0222049 A1 | 9/2009 | Frigg et al. | |
| 2009/0259226 A1 | 10/2009 | Michelson | |
| 2009/0270926 A1 | 10/2009 | Hawkes | |
| 2010/0016901 A1 | 1/2010 | Robinson | |
| 2010/0042159 A1 | 2/2010 | Butler | |
| 2010/0049256 A1 | 2/2010 | Jeon et al. | |
| 2010/0069968 A1 | 3/2010 | Assaker et al. | |
| 2010/0145459 A1* | 6/2010 | McDonough | A61B 17/86 623/17.16 |
| 2010/0234897 A1 | 9/2010 | Fisher et al. | |
| 2010/0312279 A1 | 12/2010 | Gephart et al. | |
| 2010/0312346 A1* | 12/2010 | Kueenzi | A61F 2/44 623/17.16 |
| 2011/0054528 A1 | 3/2011 | Michelson | |
| 2011/0106159 A1 | 5/2011 | Nazeck | |
| 2011/0118784 A1 | 5/2011 | Baynham et al. | |
| 2011/0190770 A1 | 8/2011 | Suh | |
| 2011/0230885 A1 | 9/2011 | Weiner et al. | |
| 2011/0313477 A1 | 12/2011 | McLean et al. | |
| 2012/0065734 A1* | 3/2012 | Barrett | A61F 2/4611 623/17.16 |
| 2012/0109208 A1 | 5/2012 | Justis et al. | |
| 2012/0179259 A1* | 7/2012 | McDonough | A61F 2/4455 623/17.16 |
| 2012/0245690 A1 | 9/2012 | Cowan, Jr. et al. | |
| 2012/0277870 A1* | 11/2012 | Wolters | A61F 2/447 623/17.16 |
| 2013/0023936 A1 | 1/2013 | Altarac et al. | |
| 2013/0046345 A1 | 2/2013 | Jones et al. | |
| 2013/0060294 A1 | 3/2013 | Donahue | |
| 2013/0245705 A1 | 9/2013 | McBride et al. | |
| 2013/0261679 A1 | 10/2013 | McBride et al. | |
| 2013/0331892 A1 | 12/2013 | Peterson et al. | |
| 2013/0345814 A1* | 12/2013 | Walkenhorst | A61B 17/7059 623/17.16 |
| 2014/0142632 A1 | 5/2014 | Keyer et al. | |
| 2014/0148860 A1 | 5/2014 | Rinner | |
| 2014/0277145 A1 | 9/2014 | Reiblat et al. | |
| 2014/0277206 A1 | 9/2014 | Reitblat et al. | |
| 2015/0039035 A1 | 2/2015 | Kruger | |
| 2016/0022317 A1 | 1/2016 | Kraus | |

FOREIGN PATENT DOCUMENTS

| | | |
|---|---|---|
| EP | 1841376 A2 | 10/2007 |
| EP | 1847229 A2 | 10/2007 |
| WO | WO2006076422 A2 | 7/2006 |
| WO | WO2007037774 A1 | 4/2007 |
| WO | WO2007101266 A1 | 9/2007 |
| WO | WO2007103081 A2 | 9/2007 |
| WO | WO2007121080 A2 | 10/2007 |
| WO | WO2006138291 B1 | 11/2007 |
| WO | WO2007134199 A2 | 11/2007 |
| WO | WO2009089395 A2 | 7/2009 |
| WO | WO2009091770 A1 | 7/2009 |
| WO | WO2009091775 A2 | 7/2009 |

* cited by examiner

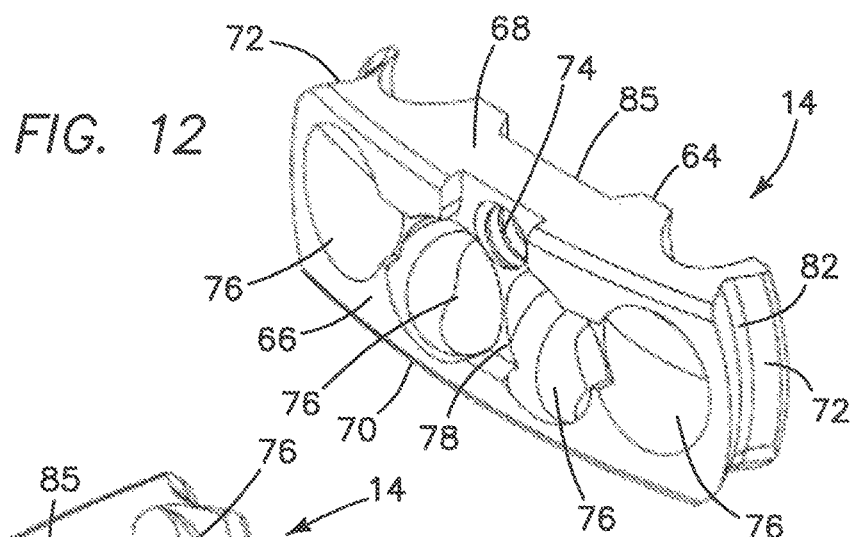
FIG. 12
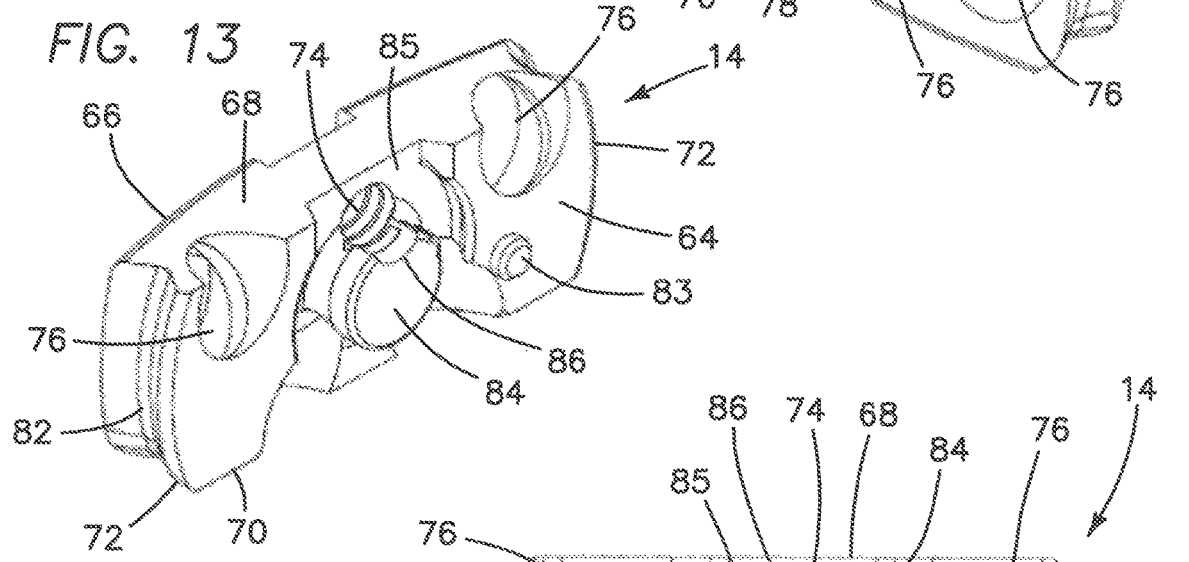
FIG. 13
FIG. 14
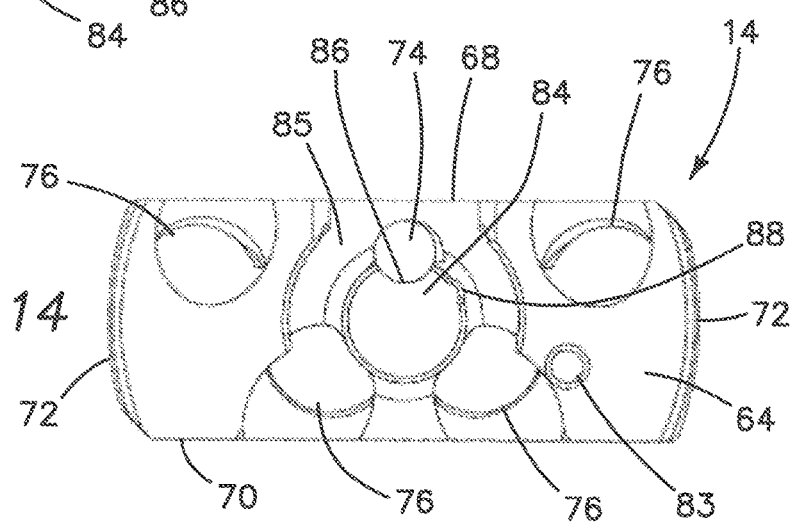
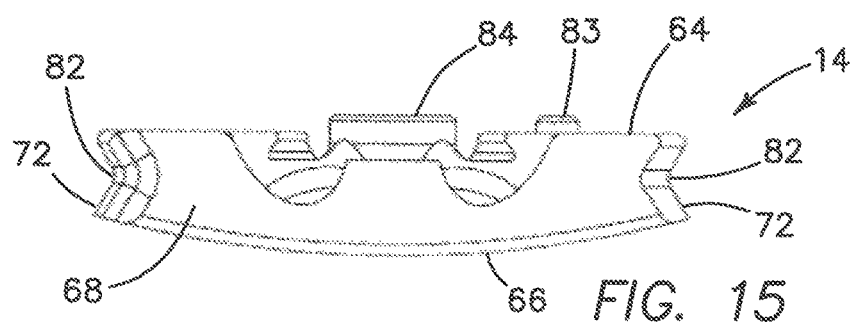
FIG. 15

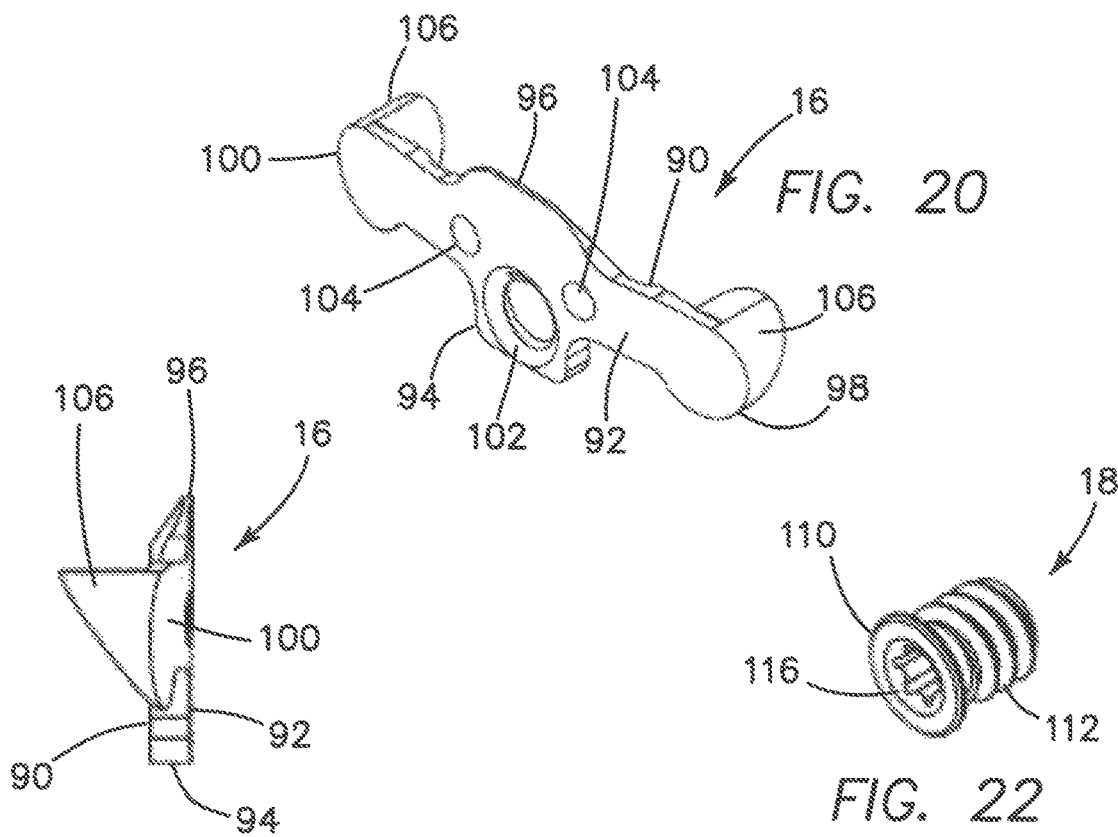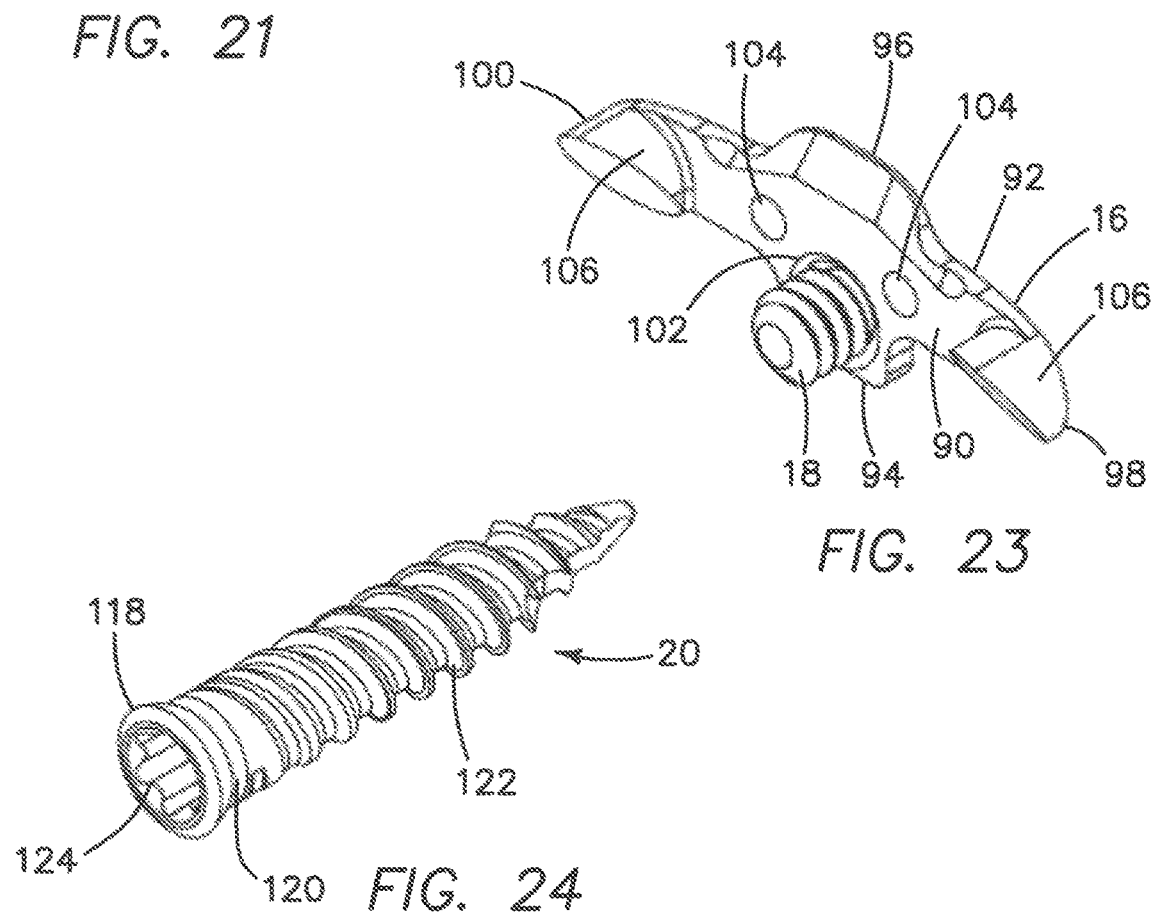

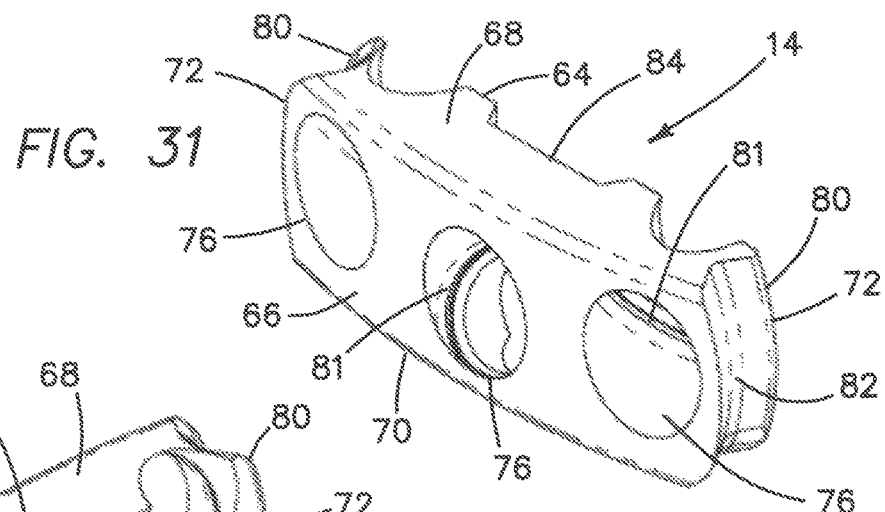
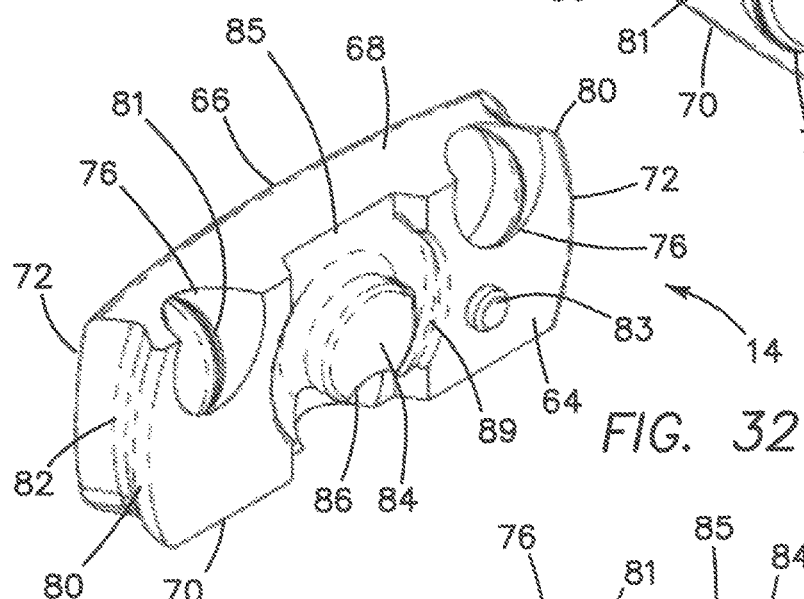
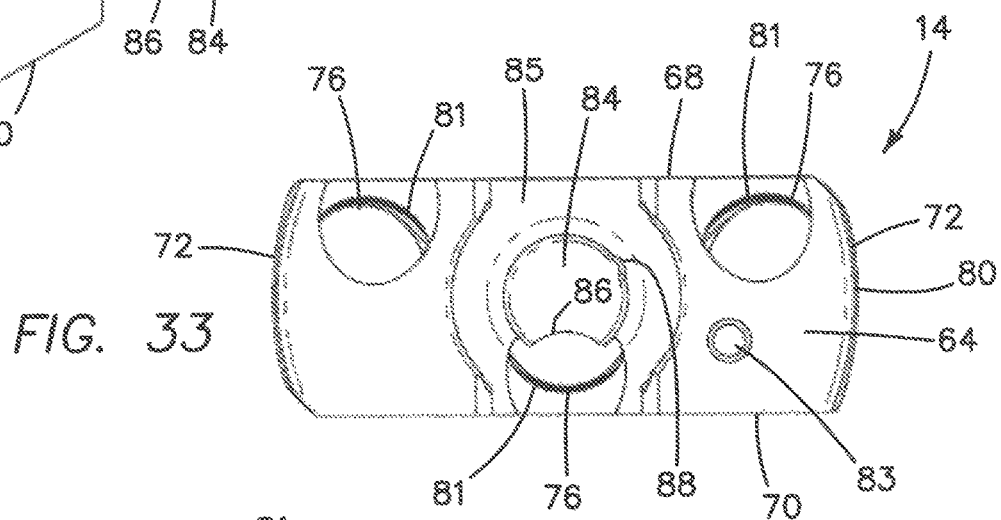
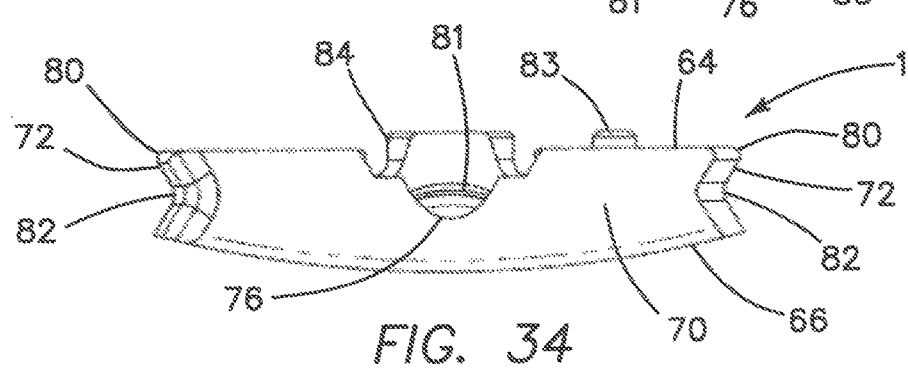

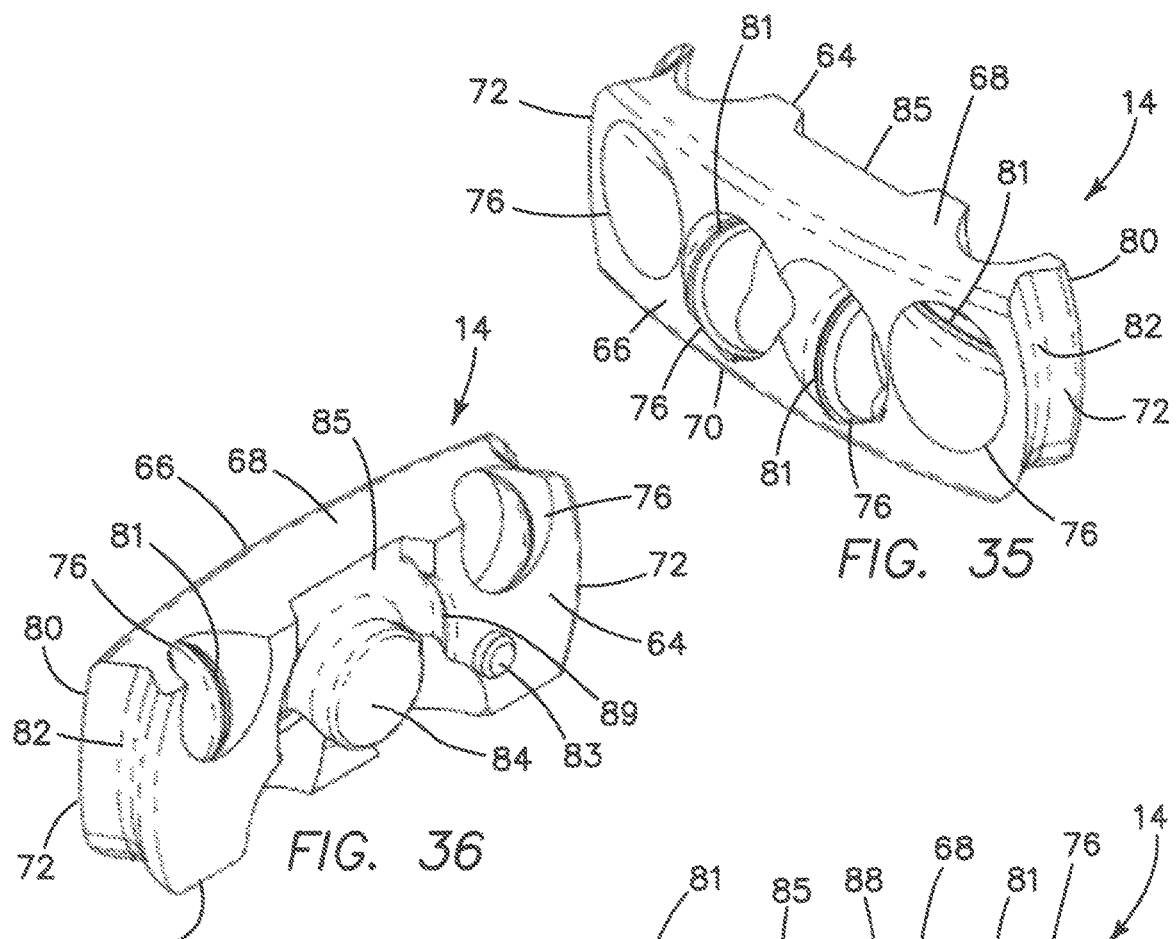
FIG. 35
FIG. 36
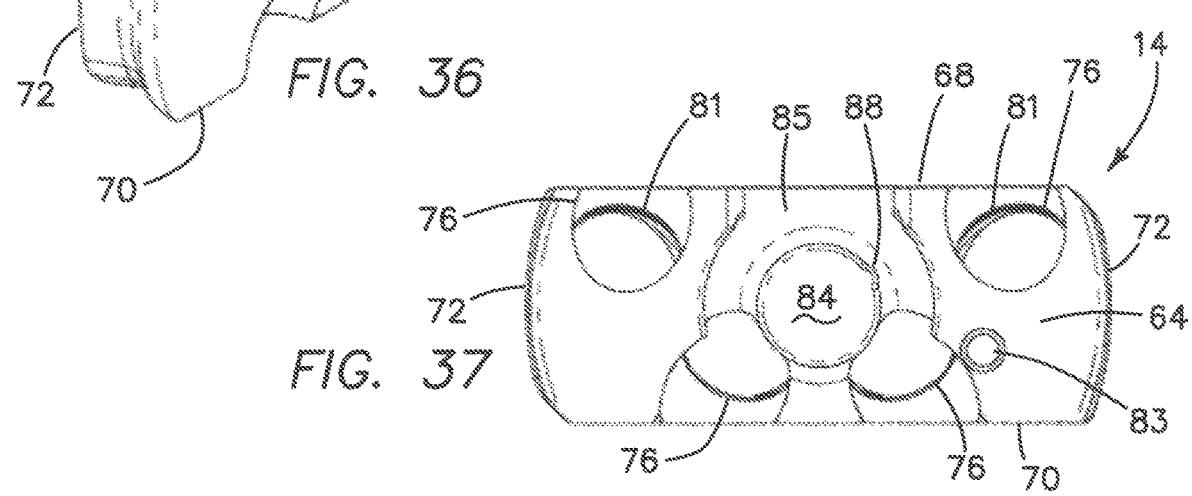
FIG. 37
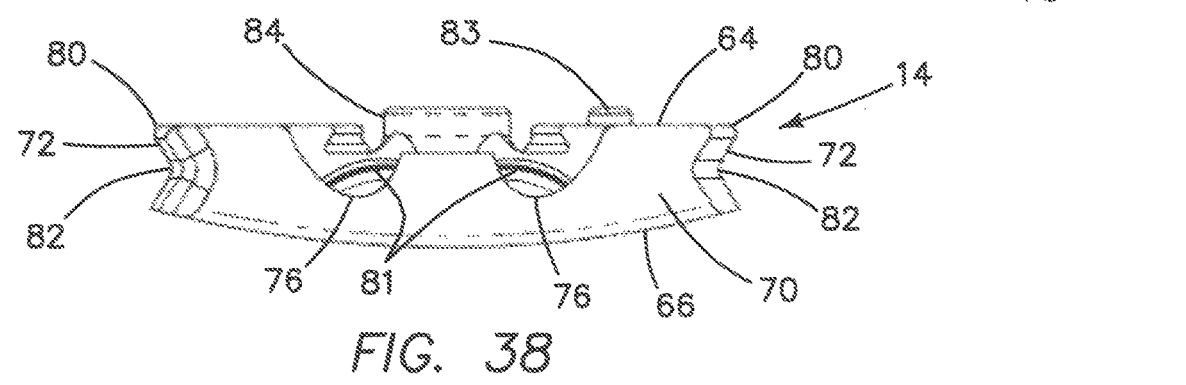
FIG. 38

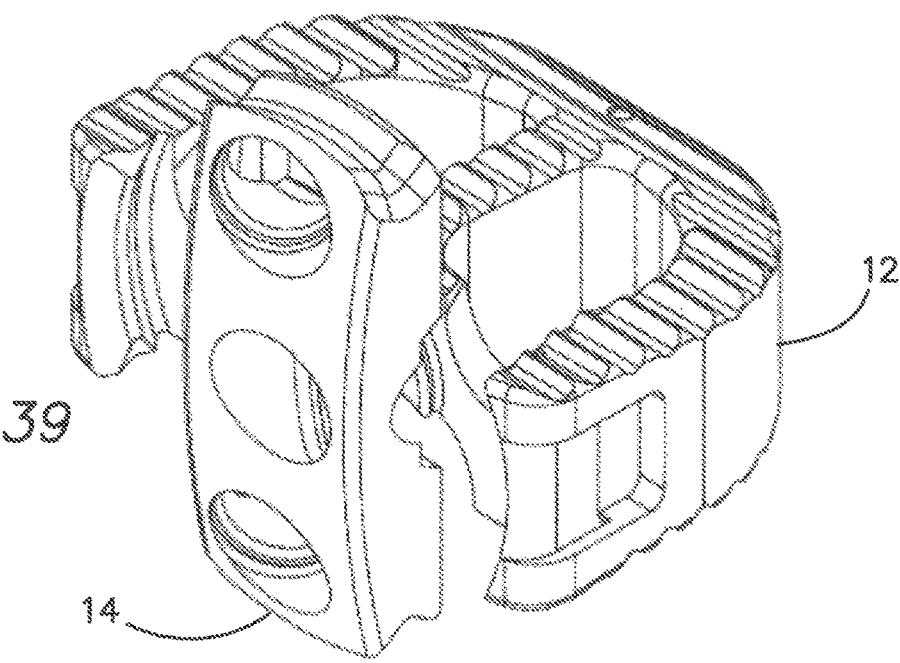
FIG. 39
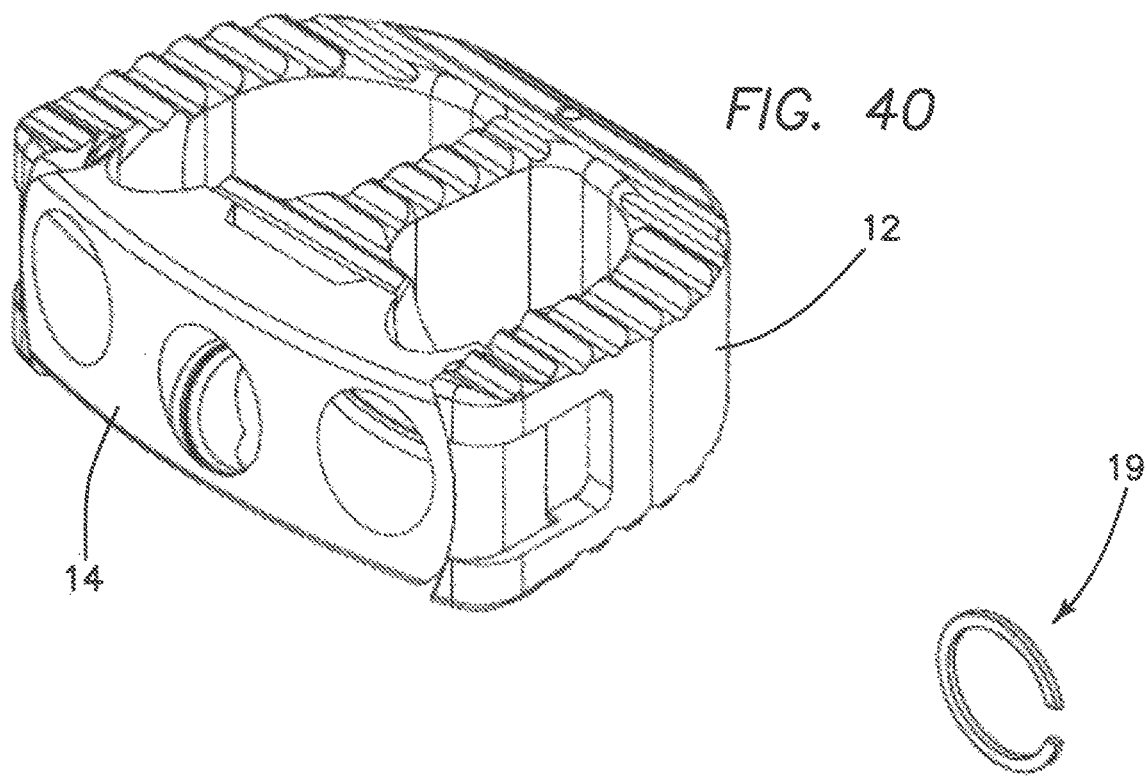
FIG. 40
FIG. 41

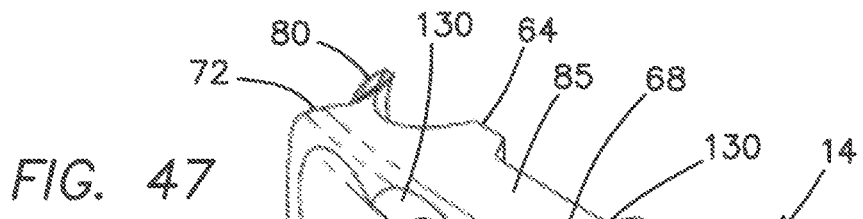
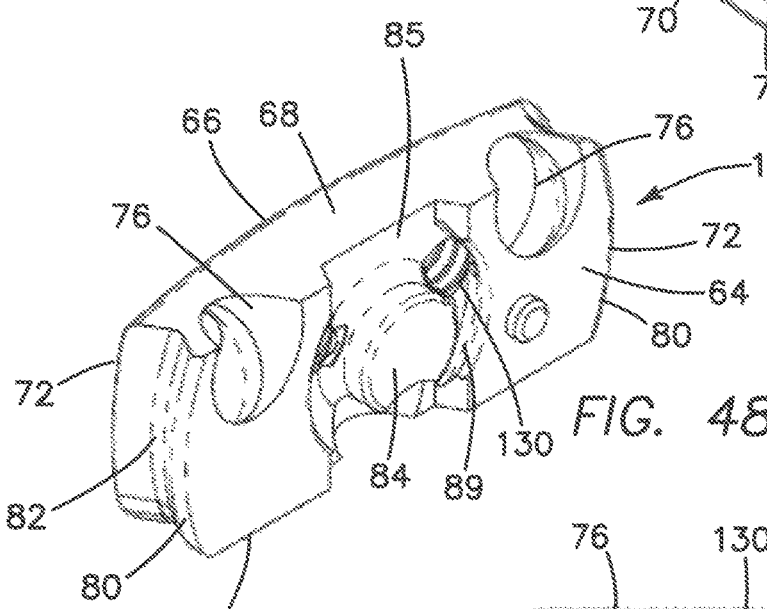
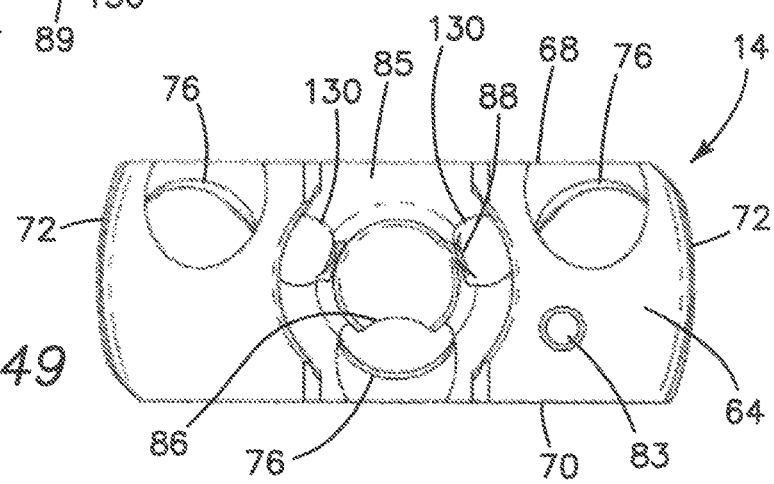
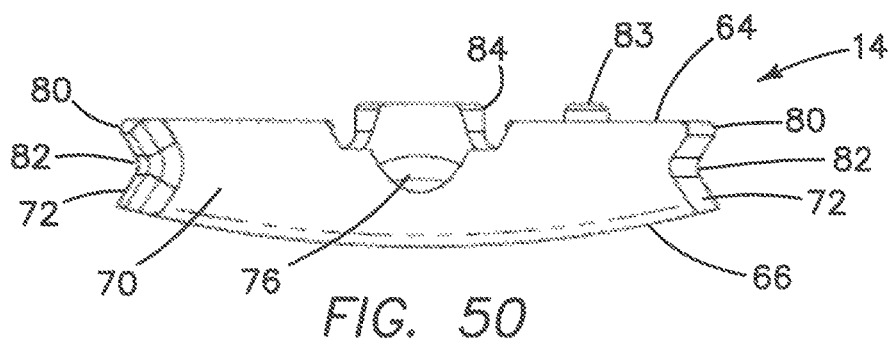

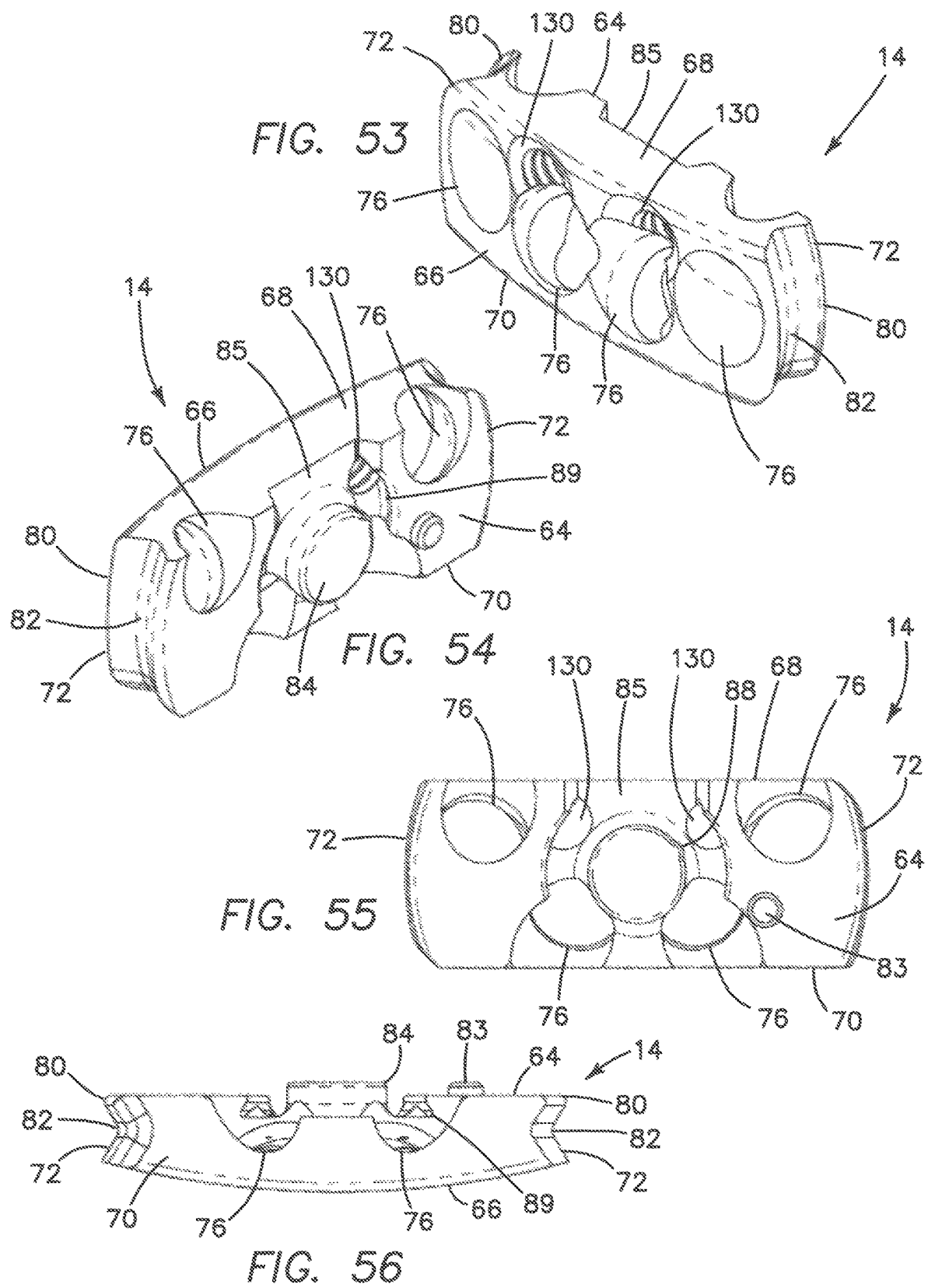

INTERBODY SPACER

FIELD OF THE INVENTION

This application relates generally to spinal implants, and in particular, intervertebral spacers and fusion cages.

BACKGROUND OF THE INVENTION

Back pain can be caused by a variety of factors including but not limited to the rupture or degeneration of one or more intervertebral discs due to degenerative disc disease, spondylolisthesis, deformative disorders, trauma, tumors and the like. In such cases, pain typically results from compression or irritation of spinal nerve roots arising from reduced spacing between adjacent vertebrae, a damaged disc and or misalignment of the spine resulting from the injury or degeneration.

Common forms of treating such pain include various types of surgical procedures in which a damaged disc may be partially or totally excised. After the disc space is prepared, one or more implants are inserted between the adjacent vertebrae in an effort to restore the natural spacing and alignment between the vertebrae, so as to relieve the compression, irritation or pressure on the spinal nerve or nerves and, thereby, eliminate or significantly reduce the pain that the patient is experiencing. Typically, one or more implants are used together with substances that encourage bone ingrowth to facilitate fusion between adjacent vertebrae and achieve immobilization of adjacent bones. Surgeons insert these intervertebral devices to adjunctively facilitate bone fusion in between and into the contiguous involved vertebrae. This fusion creates a new solid bone mass and provides weight bearing support between adjacent vertebral bodies which acts to hold the spinal segment at an appropriate biomechanically restored height as well as to stop motion in a segment of the spine and alleviate pain.

In a posterior lumbar interbody fusion (PLIF) surgery, spinal fusion is achieved in the lower back by inserting an implant such as a cage and typically graft material to encourage bone ingrowth directly into the disc space between adjacent vertebrae. The surgical approach for PLIF is from the back of the patient, posterior to the spinal column. An anterior lumbar interbody fusion (ALIF) surgical procedure is similar to the PLIF procedure except that in the ALIF procedure, the disc space is fused by approaching the spine through the abdomen from an anterior approach instead of from a posterior approach. Another fusion procedure is called a transforaminal lumbar interbody fusion (TLIF) which involves a posterior and lateral approach to the disc space. To gain access to the disc space, the facet joint may be removed whereby access is gained via the nerve foramen. In an extreme lateral interbody fusion (XLIF), the disc space is accessed from small incisions on the patient's side.

In the typical procedures described above, the adjacent vertebrae must be distracted apart by a substantial amount in order to allow the surgeon to advance the implant with relatively little resistance along the delivery path. Also, the surgeon must typically release the implant at least once as the implant is being delivered along the delivery path and align and position the implant at the target position of implantation, typically in the anterior aspect of the disc space. Once positioned, the interbody spacer is secured to the adjacent vertebrae with one or more bone screws. The implant includes apertures formed at one end for passing one or more bone screws at an upward angle into the first adjacent vertebral body and one or more bone screws at a downward angle into the second adjacent vertebral body.

Over time, the interface between the screws and the bone may present some problems of stability. Due to the anatomical structure of the spine and the extreme anatomical forces that are brought to bear on the skeleton and transmitted to the vertebral bodies, the screws securing the interbody spacer to the spine may vibrate or toggle out of position. Also, the degeneration of vertebral bone quality may result in the screws loosening or becoming dislodged. As a result, bone screws securing the plate to the spine may move or back out of the vertebral body and implant. Loosened screws may result instability of the joint and lead to increased pain for the patient.

Therefore, there is a need to provide a new and improved interbody spacer that resists fasteners, such as bone screws, from backing out and also from being loosened with respect to the implant before migrating out. Furthermore, there is a need for the implant to withstand anatomical forces and be easily implanted. Also, the screw retaining mechanism must be easily activated by the surgeon. This invention, as described in the detailed description, sets forth an improved interbody spacer that meets these needs.

SUMMARY OF THE INVENTION

According to one aspect of the invention, an interbody spacer for the spine is provided. The interbody spacer includes a cage having a top surface and a bottom surface interconnected by a sidewall. The sidewall defines a front surface of the cage. The cage includes at least two bone screw apertures. The interbody spacer includes a first screw plate connected to the cage. The first screw plate has at least two bone screw openings substantially aligned with at the least two bone screw apertures. A bone screw is inserted into each bone screw opening of the first screw plate and corresponding bone screw aperture of the cage. Each bone screw has a head at a proximal end and a threaded shank extending toward a distal end for anchoring into bone. Each bone screw is configured to secure the interbody spacer between two bony components of the spine. A first anti-backout mechanism is connected to the first screw plate and configured to prevent the bone screws from backing out relative to the first screw plate. The first screw plate is interchangeable with a second screw plate and connectable to the same cage. The second screw plate having a at least three bone screw openings for receiving at least three bone screws or different number of bone screw openings than the first screw plate and a second anti-backout mechanism.

According to another aspect of the invention, an interbody spacer for the spine is provided. The interbody spacer includes a cage having a top surface and a bottom surface interconnected by a sidewall. The sidewall defines a front surface. The cage includes at least two bone screw apertures and a longitudinal axis. The interbody spacer includes a screw plate connected to the cage. The screw plate has an inner surface and an outer surface interconnected by a top end, a bottom end and two sides. The screw plate includes at least two bone screw openings substantially aligned with the at least two bone screw apertures. The interbody spacer includes a bone screw inserted into each bone screw opening of the screw plate. Each bone screw has a head at a proximal end and a threaded shank extending toward a distal end for anchoring into bone. The head has a larger diameter than the shank. Each bone screw is configured to secure the interbody spacer to the spine. The screw plate is front loading with respect to the cage such that screw plate attaches to the cage directly from the front as opposed to being top loading.

According to another aspect of the invention, an interbody spacer for the spine is provided. The interbody spacer includes a cage having a top surface and a bottom surface interconnected by a sidewall. The sidewall defines a front surface. The cage includes a longitudinal axis and at least two bone screw apertures sized and configured to receive bone screws. The cage includes a protrusion extending outwardly from the front surface. The protrusion has an inner opening defining an inner surface and a notch formed in the inner surface. A screw plate connected to the cage. The screw plate has an inner surface and an outer surface interconnected by a top end, a bottom end and two sides. The screw plate includes at least two bone screw openings substantially aligned with the at least two bone screw apertures and sized and configured to receive bone screws. The screw plate includes a post extending outwardly from the inner surface. The post is sized and configured to be inserted into the inner opening of the protrusion. The post further includes an outwardly extending bump sized and configured to mate with the notch. The interbody spacer includes a bone screw inserted into each bone screw opening of the screw plate and configured to secure the interbody spacer to the spine. Each bone screw has a head at a proximal end and a threaded shank extending toward a distal end for anchoring into bone. The head has a larger diameter than the shank. The screw plate is attached to the front surface of the cage by rotating the screw plate with respect to the cage to bring the bump into engagement with the notch. The mating of the bump and notch is configured to prevent rotation of the screw plate relative to the cage.

According to another aspect of the invention, a bone fixation kit is provided. The kit includes a cage and a first screw plate for connecting to the cage. The first screw plate has three bone screw openings for receiving three bone screws. The kit further includes a second screw plate for connecting to the cage. The second screw plate has four bone screw openings for receiving four bone screws. The kit further includes four bone screws configured to secure the cage and one of the first screw plate and the second screw plate between two bony components of the spine.

According to another aspect of the invention, a method is provided. The method includes the step of providing an interbody spacer. The interbody spacer includes a cage having a front surface. The interbody spacer includes a first screw plate connectable to the cage. The first screw plate has three bone screw openings for receiving three bone screws. A second screw plate that is also connectable to the same cage is provided. The second screw plate has four bone screw openings for receiving four bone screws. A plurality of bone screws is provided for inserting into each bone screw opening of the first screw plate or second screw plate and configured to secure the interbody spacer to the spine. Each bone screw has a head at a proximal end and a threaded shank extending toward a distal end for anchoring into bone. The head has a larger diameter than the shank. The method includes the step of selecting one of the first screw plate and second screw plate. The method includes the step of attaching the selected screw plate to the cage. The method includes the step of inserting a bone screw into each bone screw opening.

According to another aspect of the invention, a spinal fixation system is provided. The system includes a cage, a first screw plate for connecting to the cage and a second screw plate for connecting to the cage. The first screw plate has three bone screw openings for receiving three bone screws. The second screw plate has four bone screw openings for receiving four bone screws. The system includes a plurality of bone screws configured to secure the cage and one of the first screw plate and the second screw plate between two bony components of the spine. The first screw plate and the second screw plate are interchangeable with the same cage and attached intraoperatively.

BRIEF DESCRIPTION OF THE DRAWINGS

FIG. 12 is a top frontal perspective view of a screw plate according to the present invention.

FIG. 13 is a top rear perspective view of a screw plate according to the present invention.

FIG. 14 is a rear elevational view of a screw plate according to the present invention.

FIG. 15 is a bottom planar view of a screw plate according to the present invention.

FIG. 20 is a top perspective view of a cover plate according to the present invention.

FIG. 21 is a side elevational view of a cover plate according to the present invention.

FIG. 22 is a top perspective view of a plate screw according to the present invention.

FIG. 23 is a top perspective rear view of a plate screw attached to a cover plate according to the present invention.

FIG. 24 is a top perspective view of a bone screw according to the present invention.

FIG. 31 is a top frontal perspective view of a screw plate according to the present invention.

FIG. 32 is a top rear perspective view of a screw plate according to the present invention.

FIG. 33 is a rear elevational view of a screw plate according to the present invention.

FIG. 34 is a bottom planar view of a screw plate according to the present invention.

FIG. 35 is a top frontal perspective view of a screw plate according to the present invention.

FIG. 36 is a top rear perspective view of a screw plate according to the present invention.

FIG. 37 is a rear elevational view of a screw plate according to the present invention.

FIG. 38 is a bottom planar view of a screw plate according to the present invention.

FIG. 39 is a top perspective view of a cage and a screw plate according to the present invention.

FIG. 40 is a top perspective view of cage and screw plate according to the present invention.

FIG. 41 is a top perspective view of a C-ring according to the present invention.

FIG. 47 is a top frontal perspective view of a screw plate according to the present invention.

FIG. 48 is a top rear perspective view of a screw plate according to the present invention.

FIG. 49 is a rear elevational view of a screw plate according to the present invention.

FIG. 50 is a bottom planar view of a screw plate according to the present invention.

FIG. 53 is a top frontal perspective view of a screw plate according to the present invention.

FIG. 54 is a top rear perspective view of a screw plate according to the present invention.

FIG. 55 is a rear elevational view of a screw plate according to the present invention.

FIG. 56 is a bottom planar view of a screw plate according to the present invention.

DETAILED DESCRIPTION OF THE INVENTION

Figure 1:
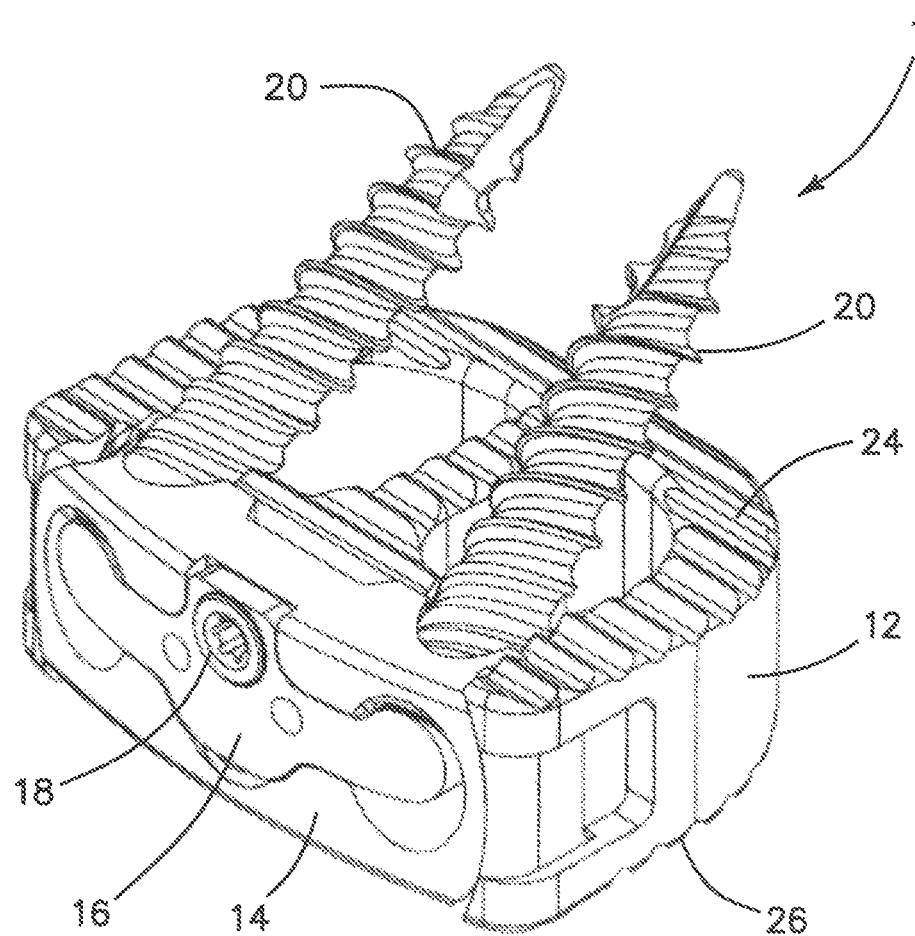
FIG. 1 is a top perspective view of an interbody spacer according to the present invention.
Figure 2:
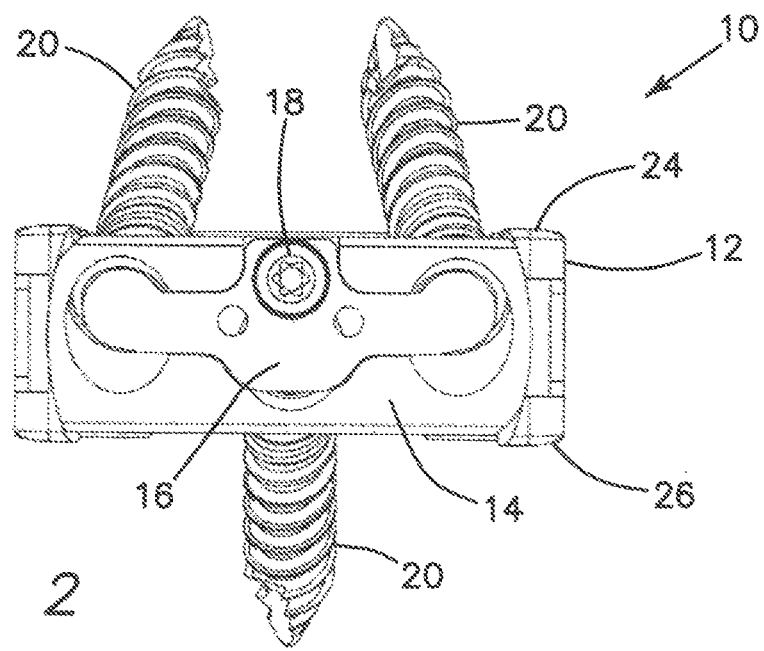
FIG. 2 is a front elevational view of an interbody spacer according to the present invention.
Figure 3:
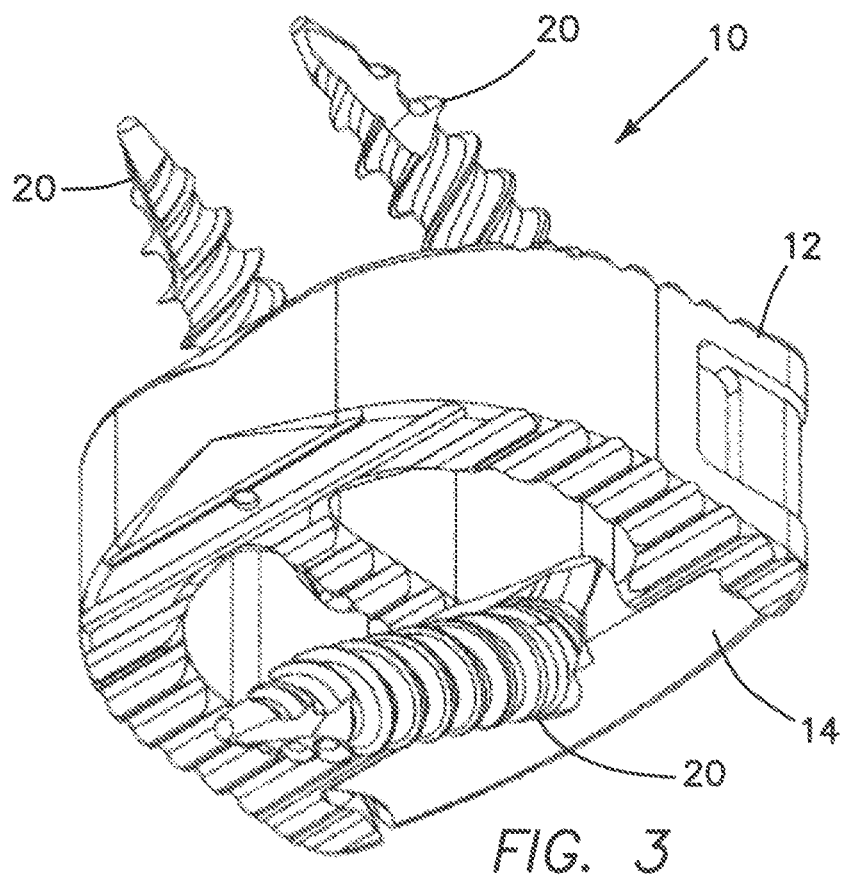
FIG. 3 is a rear, bottom perspective view of an interbody spacer according to the present invention.
Figure 4:
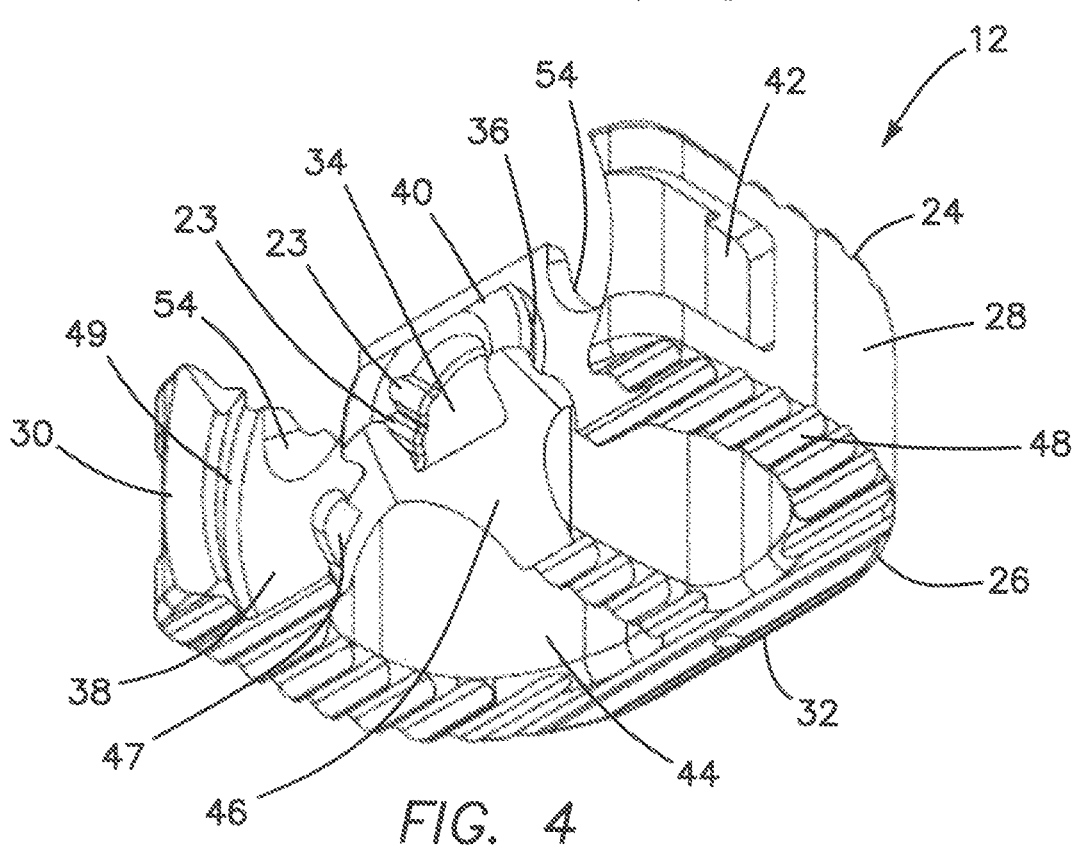
FIG. 4 is a bottom perspective view of a cage according to the present invention.
Figure 5:
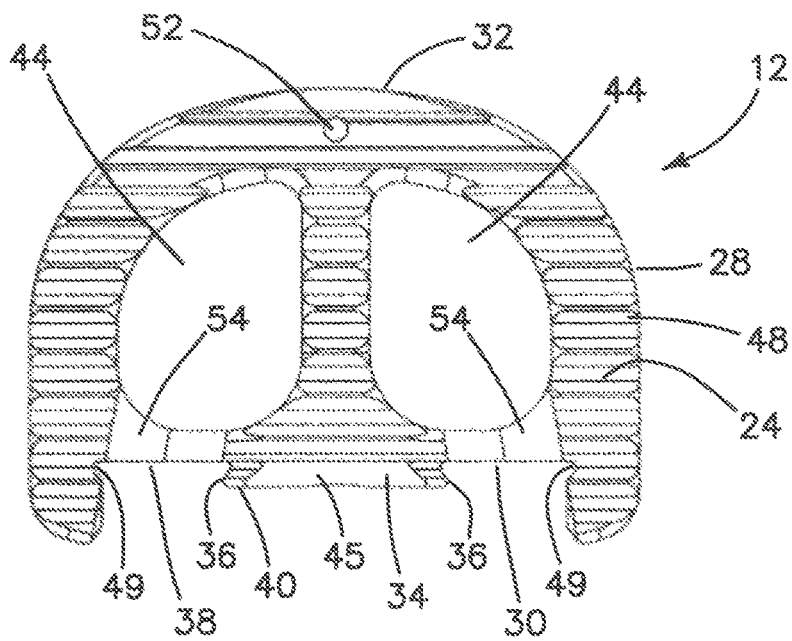
FIG. 5 is a top planar view of a cage according to the present invention.
Figure 6:
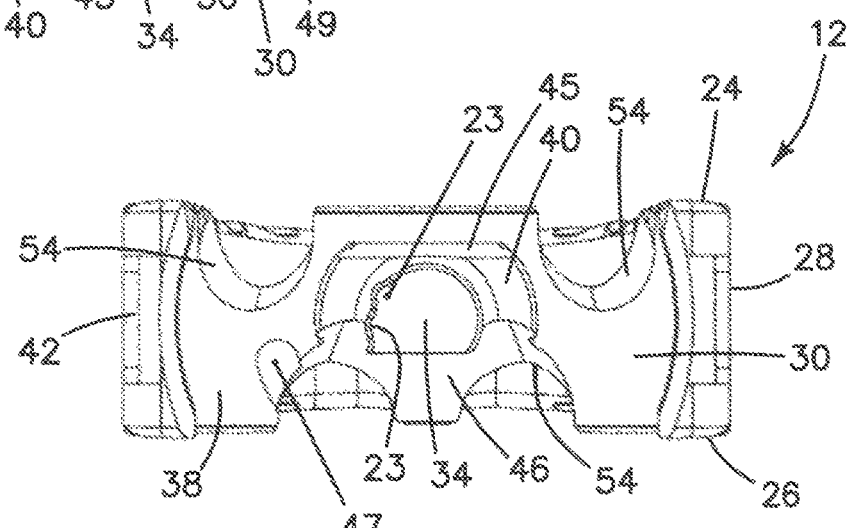
FIG. 6 is a front elevational view of a cage according to the present invention.
Figure 7:
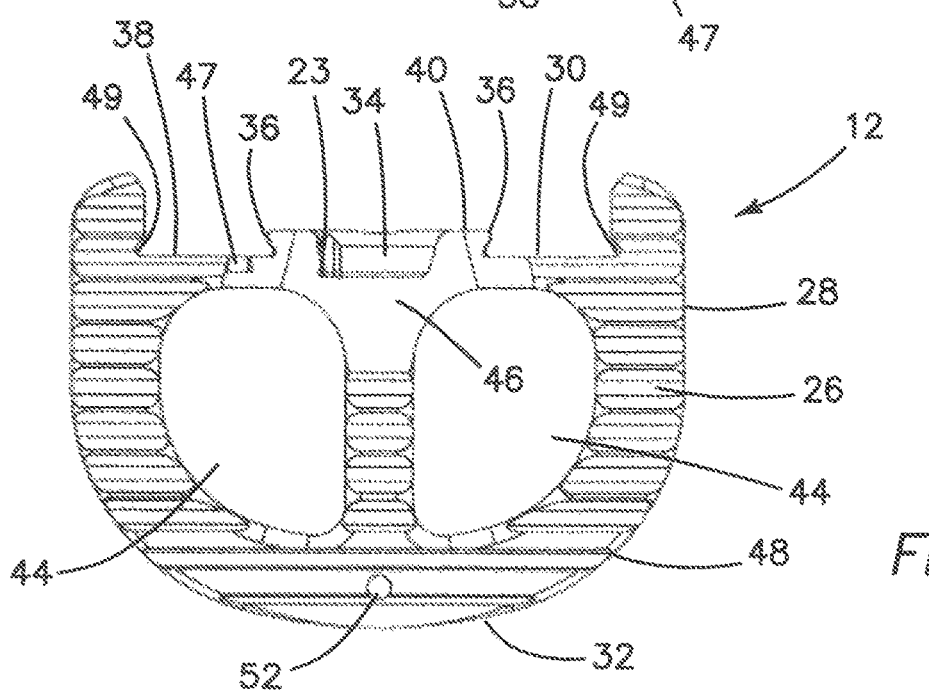
FIG. 7 is a bottom planar view of a cage according to the present invention.
Figure 8:
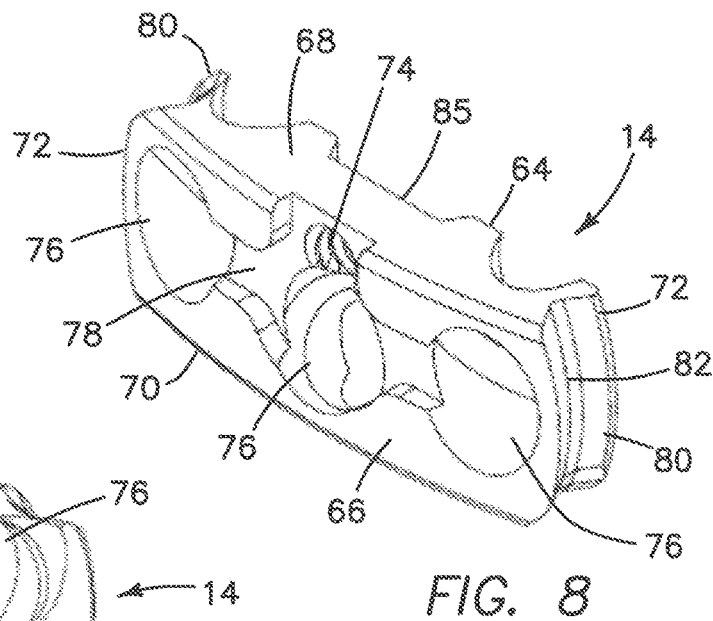
FIG. 8 is a top frontal perspective view of a screw plate according to the present invention.
Figure 9:
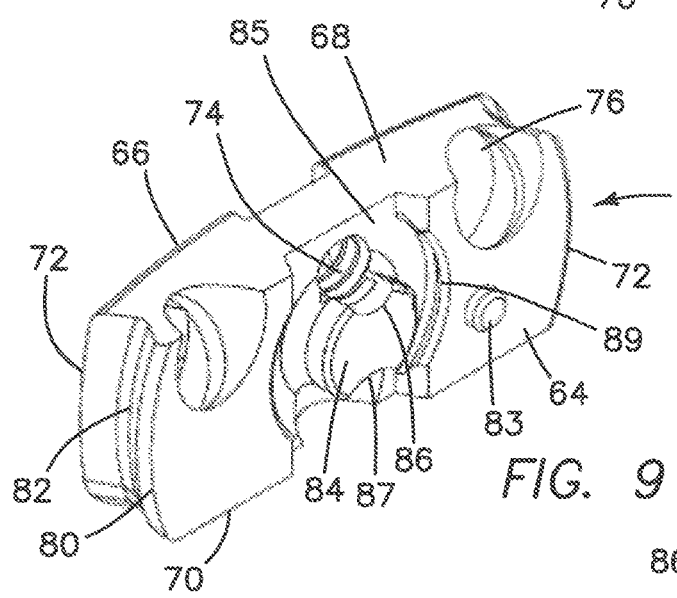
FIG. 9 is a top rear perspective view of a screw plate according to the present invention.
Figure 10:
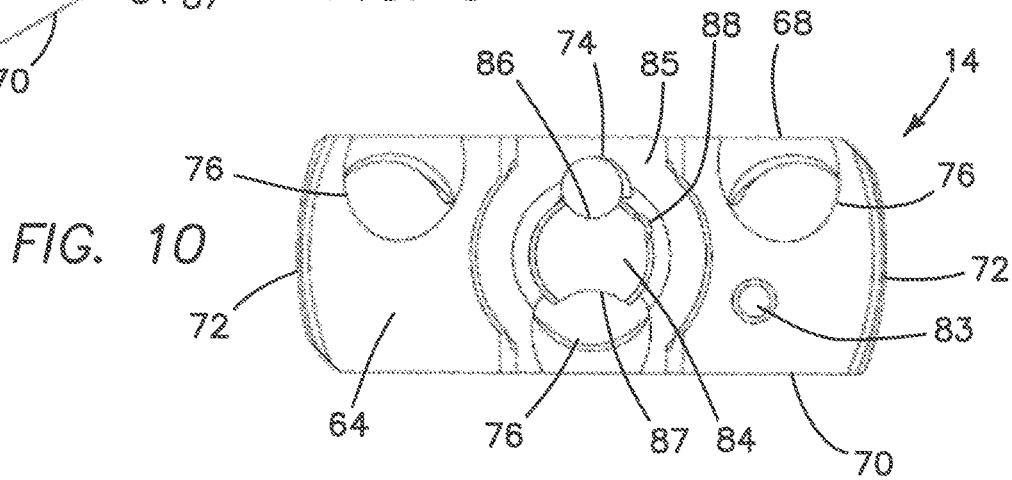
FIG. 10 is a rear elevational view of a screw plate according to the present invention.
Figure 11:
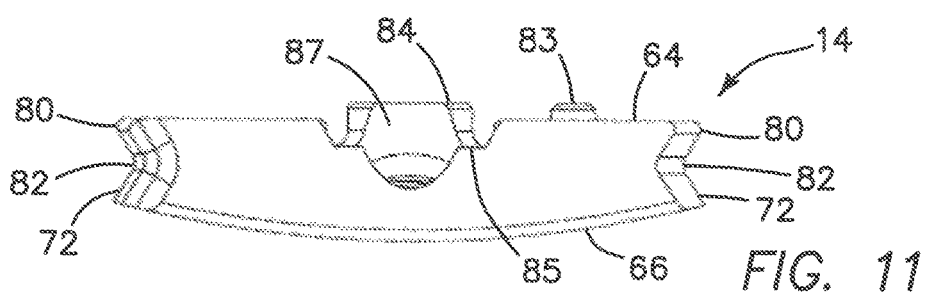
FIG. 11 is a bottom planar view of a screw plate according to the present invention.

FIGS. 1-3 depict an interbody spacer 10 according to one variation of the invention that may be used to stabilize or fuse vertebral bodies in the lumbar or other region of the spine. The interbody spacer 10 comprises a cage 12, a screw plate 14, a cover plate 16, a plate screw 18, and bone screws 20. The screw plate 14 is connected to the cage 12 to receive a plate screw 18 to secure the cover plate 16 to the cage 12 in order to retain the bone screws 20 disposed in the cage 12. The bone screws 20 are configured relative to the cage to anchor the interbody spacer 10 between two bony components of the spine. Optional radiographic markers are embedding within the cage 12.

Turning now to the FIGS. 4-7, the cage 12 will now be described in greater detail. The cage 12 includes a top surface 24 and a bottom surface 26 interconnected by at least one sidewall 28 extending between the top surface 24 and the bottom surface 26 defining a cage height. The cage 12 has a shape that mimics a spinal disc. The sidewall 28 has an anterior surface 30 and a posterior surface 32 interconnected by two side surfaces. The anterior surface 30 has a larger cage height relative to the posterior surface 32 imparting the cage 12 with a slight wedge-like configuration having a taper from the anterior surface 30 to the posterior surface. This taper is designed to accommodate the natural anatomic relationship between adjacent vertebral bones and maintain the normal lordotic curvature of the spine. The cage 12 has a lordotic angle that is between approximately 5 degrees and 15 degrees. The cage 12 has a cage height of approximately 10-20 mm such as approximately 12 mm, 14 mm, 16 mm and 18 mm. The anterior and posterior surfaces 30, 32 are longer than the side surfaces when measured along a lateral dimension giving the cage 12 an elongate shape when viewed along the longitudinal axis. The lateral dimension of the cage 12 as measured between side surfaces is approximately 25 mm-40 mm and the anterior-to-posterior dimension is approximately 20 mm-30 mm. The intersections of the surfaces are smooth and rounded giving the cage 12 an overall oval or oblong shape.

The anterior surface 30 of the cage 12 includes a screw plate recess 38. The screw plate recess 38 is sized and configured to conform to and to receive the screw plate 14. When the screw plate 14 is attached to the cage 12, the screw plate 14 is recessed such that the screw plate 14 does not significantly protrude or extend outwardly from the anterior surface 30. In one variation, the depth of the screw plate recess 38 substantially equals the thickness of the screw plate 14 such that the screw plate 14 is flush with the anterior surface 30 when attached to the cage 12. Within the screw plate recess 38, a protrusion 40 is formed. The protrusion 40 extends from the floor of the screw plate recess 38. The protrusion 40 includes an outer surface and an inner surface. The inner surface of the protrusion 40 defines an opening 34. The opening 34 includes at least one notch 23 formed on the inner surface that is sized and configured to mate with a corresponding bump on the screw plate 14 that together with the notch 23 serve as a locking mechanism between the cage 12 and the screw plate 14 that will be discussed in greater detail below. The notch 23 extends along the length of the longitudinal axis of the protrusion 40. The outer surface of the protrusion 40 defines a tongue 36 near the floor of the cover plate recess 38. The groove 36 is sized and configured to mate with a tongue on the screw plate 14. The protrusion 40 includes curved sides that include the groove 36, a substantially flat top 45 and angled bottom 46. The angled bottom 46 accommodates the bone screws 20. The screw plate recess 38 further includes a stop 47 formed as a groove or a recess in the floor of the screw plate recess 38. The stop 47 is configured to mate with a correspondingly-shaped protrusion on the screw plate 14, is sized and configured to receive at least a portion of the screw receiver 14 such that the screw receiver 14 does not protrude or extend into the cover plate recess 38 as doing so would prevent the cover plate 16 from seating neatly within the cover plate recess 38. The outer perimeter of the screw plate recess 38 also includes a groove 49 for mating the cage 12 with the screw plate 14. The cage 12 includes bone screw apertures 54 sized and configured for receiving and permitting angulation of the bone screws 20.

The side surfaces cage 12 each include instrument notches 42 which serve as tool receiving recesses that are sized and configured to receive oppositely disposed distal prongs of an insertion instrument used for delivering, implanting and removing the interbody spacer 10. The instrument notches 42 are formed laterally oppositely from each other near the lateral axis of the cage 12. The instrument notches 42 may include a ramped surface such that the prongs of an insertion instrument do not unduly extend laterally outwardly from the side surfaces.

The top surface 24 or superior surface of the cage 12 is configured for engaging a lower endplate of a first vertebral bone and the bottom surface 26 or inferior surface of the cage 12 is configured for engaging an upper endplate of an adjacent second vertebral bone of the spine. The top and bottom surfaces 24, 26 are spaced apart with the sidewall 28 extending therebetween. The top and bottom surfaces 24, 26 define a longitudinal axis extending substantially normal to the top and bottom surfaces 24, 26. It is understood that the longitudinal axis is not precisely normal to the top and bottom surfaces 24, 26 due to the narrowing height and lordotic angle of the cage 12 from the anterior surface 30 to the posterior surface 32. The longitudinal axis of the cage 12 is approximately parallel to or substantially coaxial with the longitudinal direction of the spine when the interbody spacer 10 is implanted. Extending between the top surface 24 and the bottom surface 26 is at least one central cage opening 44 having an opening at the top surface 24 and extending to an opening at the bottom surface 26. The central cage openings 44 reduces the weight of the cage 12 and permit bone ingrowth to take place into and through the cage 12. A family of bone graft materials, such as autograft, bone morphogenic protein (BMP), bone marrow aspirate, concentrate, stem cells and the like, may be placed inside the central cage openings 44 to promote bone growth into the cage 12. A plurality of ridges 48 are formed on the top surface 24 and the bottom surface 26. The ridges 48 have pointed peaks to engage and increase the purchase on the endplates of adjacent vertebra. The ridges 48 may further be angled with respect to the top and bottom surfaces 24, 26 such that the ridges 48 help to hold and prevent migration of the cage 12 relative to the adjacent vertebrae when implanted within the intervertebral space. The top surface 24 and/or the bottom surface 26 of the cage 12 may include one or more radiographic pin holes 52 for receiving radiographic markers.

Turning now to FIGS. 8-15, the screw plate 14 will now be described in greater detail. The screw plate 14 serves as an interface for receiving the cover plate 16 and plate screw 18. The screw plate 14 includes an inner surface 64 and an outer surface 66 interconnected by a top end 68, bottom end 70 and sides 72. The screw plate 14 is configured for attachment to the cage 12 and, in particular, for attachment to the anterior surface 30 of the cage 12. The screw plate 14 has curved contour that matches the curvature of the cage sidewall 28 and is sized and configured to fit within the screw plate recess 38 such that the outer surface 66 is flush with the outer surface of the cage 12. The screw plate 14 includes a threaded plate screw aperture 74 configured to receive a plate screw 18 to attach the cover plate 16 to the screw plate 14 and in turn to the cage 12. The plate screw aperture 74 is located along the midline of the screw plate 14. The screw plate 14 includes one or more bone screw openings 76 sized and configured to receive bone screws 20 in a manner that permits their polyaxial angulation with respect to the screw plate 14 and cage 12. With the screw plate 14 in position and attached to the cage 12, the bone screw openings 76 are substantially aligned with the bone screw apertures 54 formed in the cage 12. One or more bone screw openings 76 are angled toward the top surface 24 such that bone screws 20 inserted therein are directed into the lower endplate of the adjacent upper vertebra. Two bone screw openings 76 are shown angled upwardly toward the upper vertebral body in the variation of FIGS. 1-3 and 8-11. One or more bone screw openings 76 are angled toward the bottom surface 26 such that bone screws 20 inserted therein are directed into the upper endplate of the adjacent lower vertebra. One bone screw opening 76 is shown angled downwardly toward the lower vertebral body in the variation of FIGS. 1-3 and 8-11. The bone screw opening 76 that is angled downwardly is formed between the two bone screw openings 76 that are angled upwardly and substantially along the midline of the cage 12. In the variation shown in FIGS. 12-15 and 25-26, two bone screw openings 76 are shown angled upwardly toward the upper vertebral body and two bone screw openings 76 are shown angled downwardly toward the lower vertebral body. Each bone screw opening 76 includes an interior ledge for contact with the head of the bone screw 20. The interior ledge divides the bone screw opening 76 into a bone screw shaft receiving portion and a bone screw head receiving portion. The inner diameter of the head receiving portion is larger than the inner diameter of the shaft receiving portion to accommodate the relatively larger head of the bone screw 20 and to permit it to angulate substantially polyaxially. The bone screw openings 76 are fluted to accommodate the polyaxial range of angulation of the bone screw 20 with respect to the cage 12. All of the bone screw openings 76 are formed in the location of the cover plate recess 78 such that when the cover plate 16 is installed, it covers all of the bone screws 20 inserted therein to prevent them from backing out of the cage 12.

The screw plate 14 further includes a cover plate recess 78 recessed down from the outer surface 66 at the anterior side. The cover plate recess 78 is sized and configured to receive the cover plate 16 such that the cover plate 16 is substantially flush with the outer surface 66 when the cover plate 16 is located inside the cover plate recess 78. Each of the sides 72 of screw plate 14 includes a tongue 80 near the inner surface 64 and a groove 82 sized and configured to mate with the groove 49 on the cage 12. The inner surface 64 of the screw plate 14 includes a post 84 extending outwardly from a recess 85 with respect to the inner surface 64. The post 84 is sized and configured to fit inside the inner opening 34 in the protrusion 40 of the cage 12. The post 84 is substantially cylindrical in shape and includes at least a first scallop 86 at the top to accommodate a plate screw 18. A second scallop 87 may be formed at the bottom to accommodate a bone screw 20 if needed. The outer surface of the post 84 includes a bump 88 to serve as a locking mechanism when engaged with the notch 23 inside the protrusion 40 of the cage 12. The edges of the recess 85 are curved and sized and configured to receive the protrusion 40 of the cage 12. The edges of the recess 85 also include a groove 89 best seen in FIG. 9. The groove 89 is sized and configured to receive the tongue 36 on the protrusion 40 of the cage 12. The configuration is generally a tongue 36 and groove on the protrusion 40 that is configured to mate with the tongue and groove 89 on the inside edges of the recess 85 of the screw plate 14. The screw plate 14 further includes a protuberance 83 extending outwardly from the inner surface 64 of the screw plate 14. The protuberance 83 is substantially cylindrical and sized and configured to fit inside and abut the stop 47 on the cage 12. The screw plate 14 is typically made of biocompatible metal such as polyether ether ketone (PEEK), stainless, surgical steel, titanium and any other suitable material. As shown in FIGS. 8-11, the screw plate 14 is designed with three bone screw openings 76 to receive three bone screws 20 for anchoring the cage 12 into adjacent vertebrae. An alternative variation is shown in FIGS. 12-15 where like reference numbers are used to describe like parts. The screw plate 14 of FIGS. 12-15 is includes four bone screw openings 76 in order to receive four bone screws 20 for anchoring the cage 12 into adjacent vertebrae. The screw plate 14 of FIGS. 8-11 and the screw plate of FIGS. 12-15 are advantageously interchangeable with the same cage 12 of FIGS. 4-7. It is up to surgeon preference which screw plate 14 to employ for a given anatomy. The surgeon is provided with both a three-bone-screw screw plate and a four-bone-screw screw plate, both of which can be advantageously mounted on the same cage 12 that the surgeon is using without having to remove the cage 12 or have a second cage 12 on hand that will accommodate more or fewer bone screws. Hence, the surgeon can decide during surgery how many bone screws 20 are necessary for a given anatomy given the uniqueness of each vertebrae and varying fragility of the bone. The surgeon simply choses the appropriate screw plate 14 either for accommodating three or four bone screws 20 and proceeds to mount the desired screw plate 14 on the cage 12. Advantageously, if the surgeon decides to implant a different number of bone screws 20, the screw plate 14 is easily removed and another screw plate with more or fewer bone screw openings 76 is mounted onto the cage 12. The mounting of the screw plate 14 onto the cage 12 will be described in greater detail below.

Figure 16:
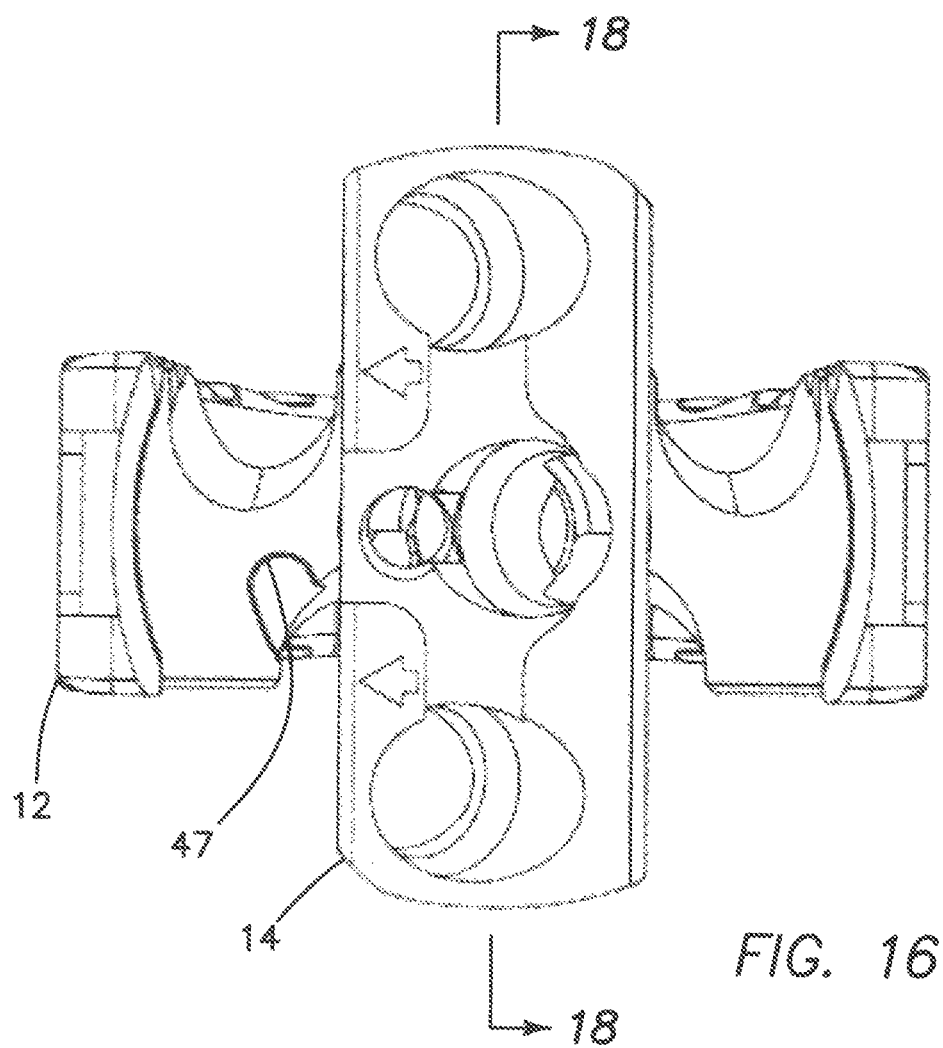
FIG. 16 is a front elevational view of a cage and a screw plate according to the present invention.
Figure 17:
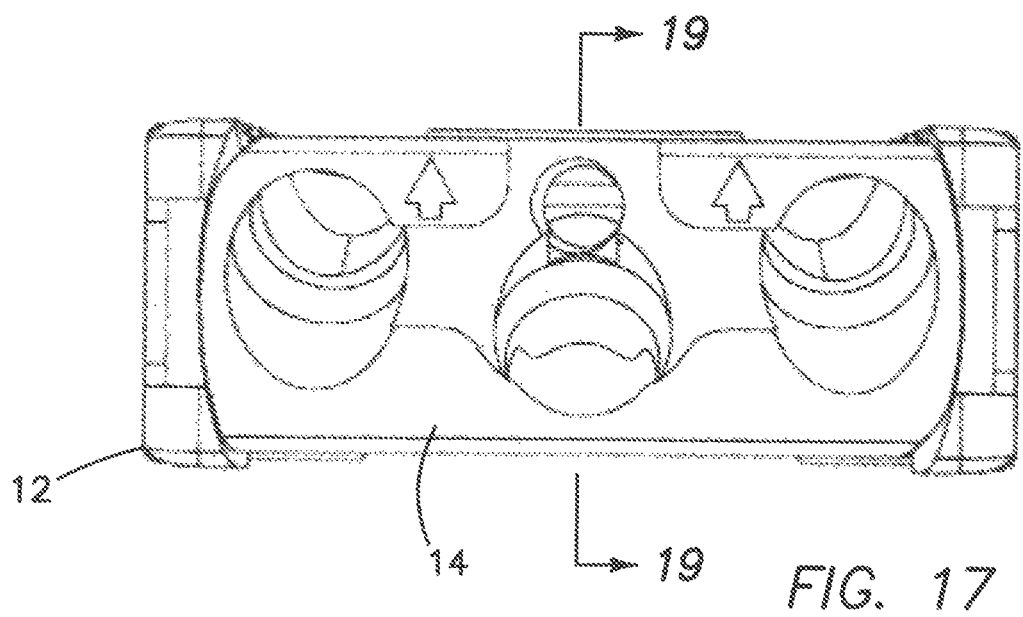
FIG. 17 is a front elevational view of cage and screw plate according to the present invention.
Figure 18:
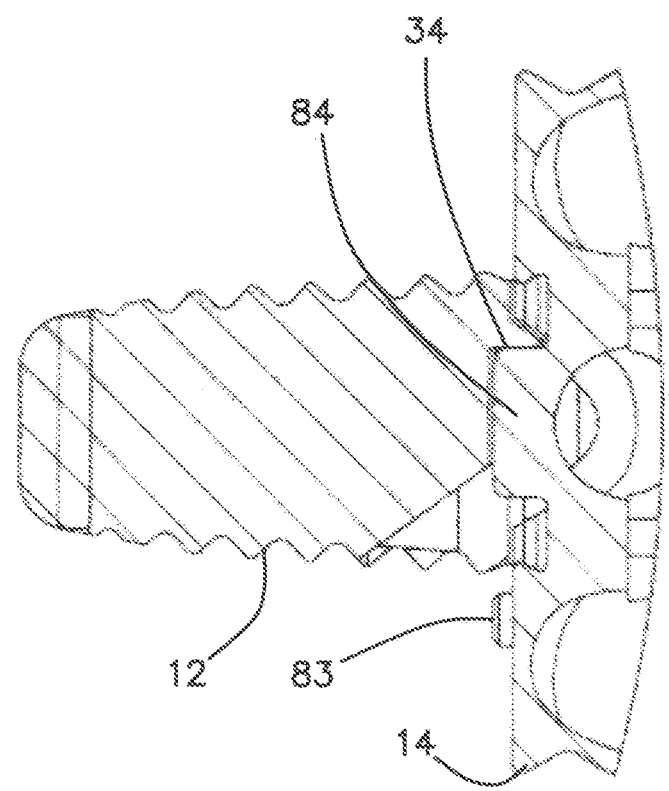
FIG. 18 is a cross-sectional view taken along line 18-18 of FIG. 16 of a cage and screw plate according to the present invention.
Figure 19:
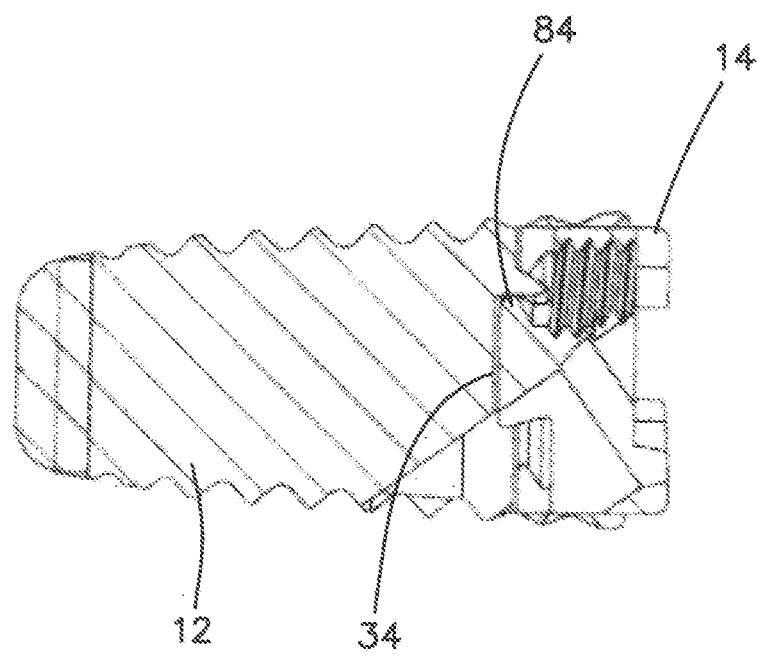
FIG. 19 is a cross-sectional view taken along line 19-19 of FIG. 17 of a cage and screw plate according to the present invention
Figure 25:
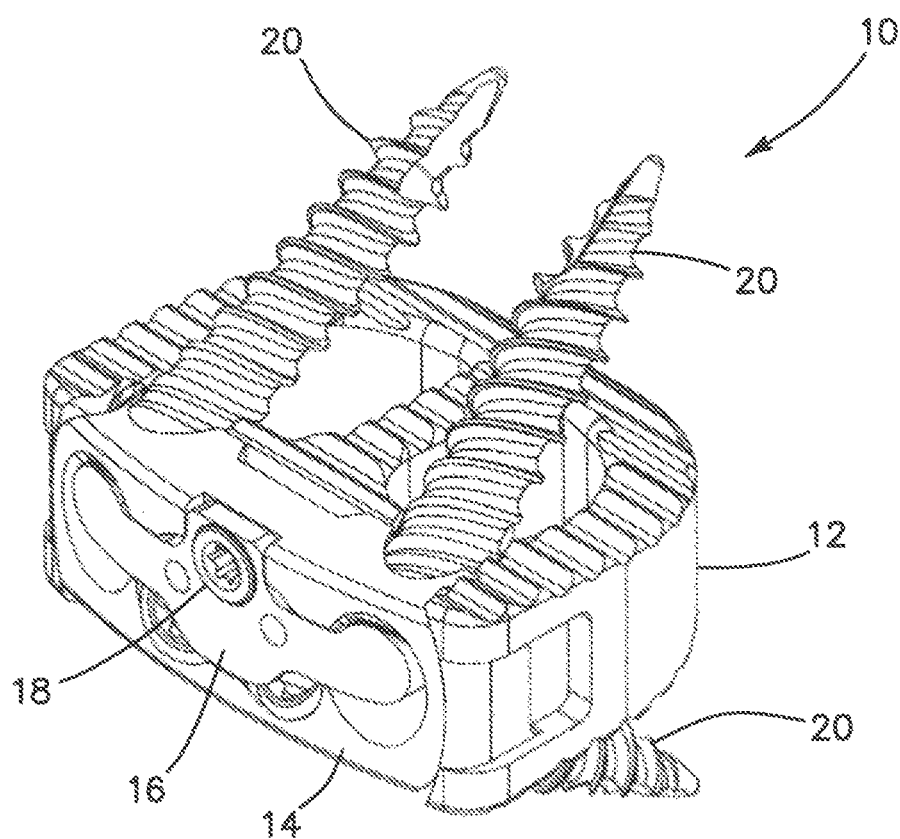
FIG. 25 is a top perspective view of an interbody spacer according to the present invention.
Figure 26:
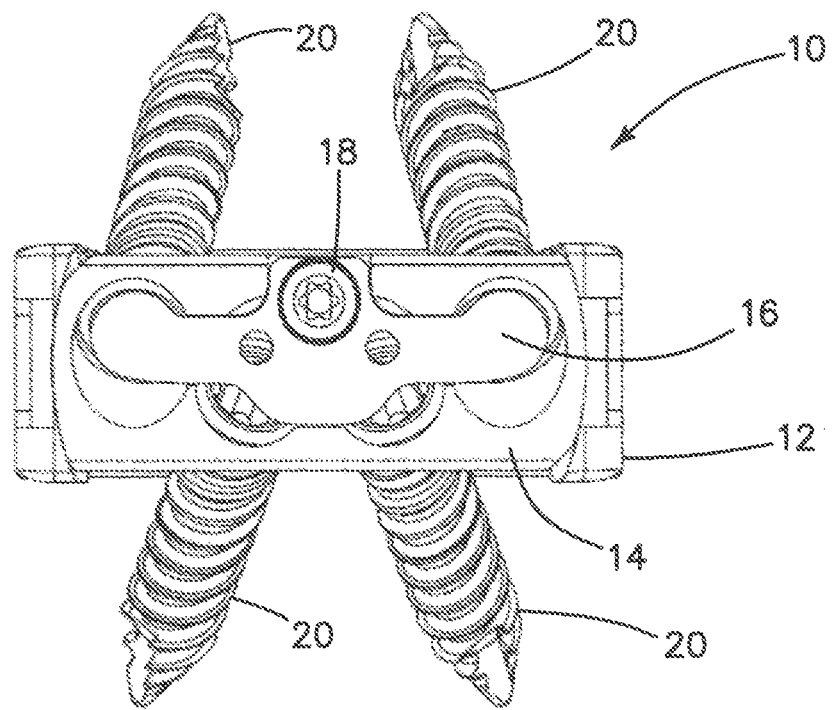
FIG. 26 is a front elevational view of an interbody spacer according to the present invention.
Figure 27:
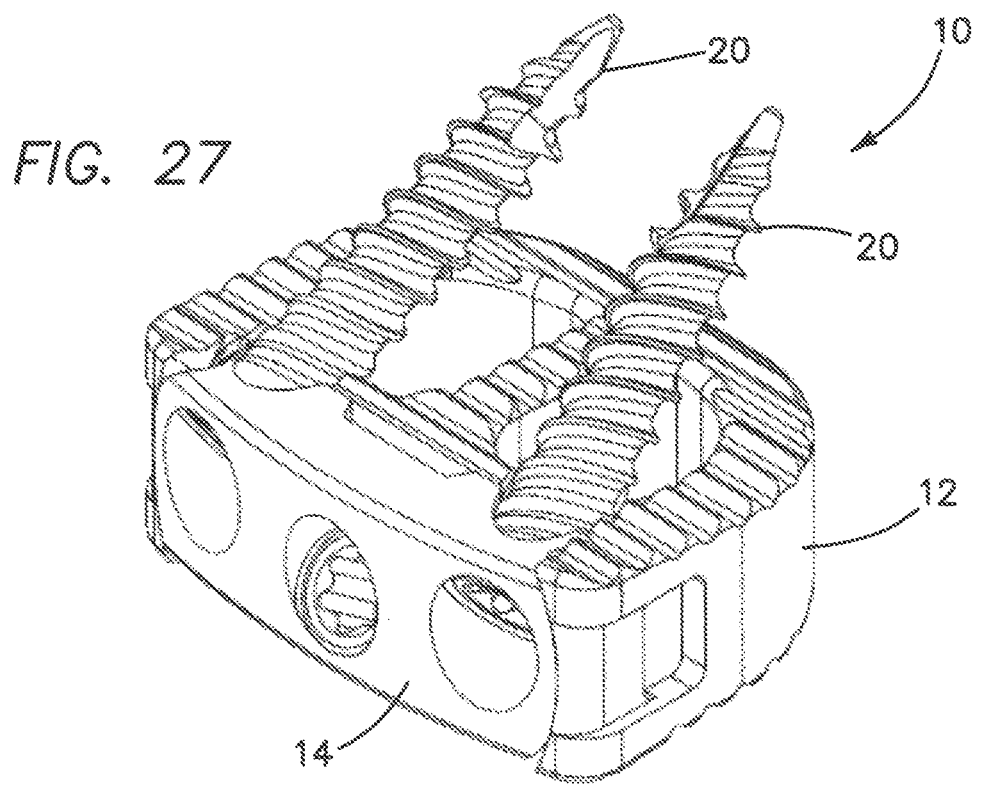
FIG. 27 is a top perspective view of an interbody spacer according to the present invention.
Figure 28:
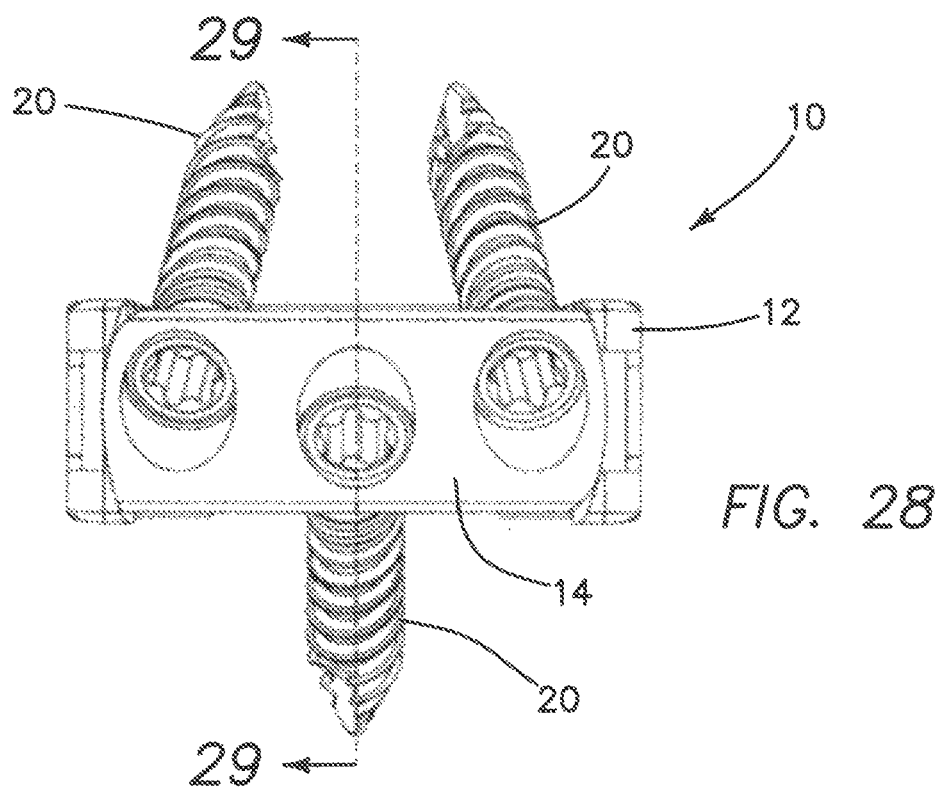
FIG. 28 is a front elevational view of an interbody spacer according to the present invention.

Turning now to FIGS. 16-19, the mounting of the screw plate 14 onto the cage 12 will now be described. The screw plate 14 is oriented at approximately 90 degrees with respect to the cage 12 as shown in FIG. 16. The post 84 on the screw plate 14 is inserted into the inner opening 34 on the cage 12 as can be seen in FIG. 18. The tongue 80 and groove 82 on the sides 72 as well as the groove 89 at the edge of the recess 85 are clear from correspondingly mating groove 49 and tongue 36 on the cage 12. The screw plate 14 is then rotated with respect to the cage 12 by approximately 90 degrees in a clockwise direction as viewed from the anterior direction toward the outer surface 66 of the screw plate 14. As the screw plate 14 is rotated, the tongue 80 on the sides of the screw plate 14 will slide into the groove 49 on the cage 12 and with the rotation, the tongue 36 on the cage 12 will slide into groove 89 on the screw plate 14. Directional indicators such as arrows are provided on the outer surface 66 of the screw plate 14 to provide an indication to user which side of the screw plate 14 should face up. With the help of the directional indicators, the user then rotates the screw plate 14 with respect to the cage 12 in the proper clockwise direction into a position shown in FIGS. 17 and 19. The rotation is stopped by the protuberance 83 on the screw plate 14 coming into contact and abutting the stop 47 formed on the cage 12. Also, the bump 88 on the post 84 will snap into the notch 23 on the inner surface of the protrusion 40 to serve as a locking mechanism preventing the rotation of the screw plate 14 with respect to the cage 12. The bump 88 and notch 23 interface prevents the counter-clockwise rotation of the screw plate 14 and the mating of the tongues and grooves prevent the screw plate 14 from detaching away from the cage 12. These two mechanisms advantageously secure the screw plate 14 to the cage 12. If the user wishes to remove the screw plate 14 from the cage 12, the user would rotate the screw plate 14 in a counter-clockwise direction with sufficient force to overcome the engagement of the notch 23 and bump 88 and further by approximately 90 degrees to disengage the mating of the tongues and grooves. With the screw plate 14 removed, the user may advantageously substitute the removed screw plate 14 with another screw plate 14, such as the one having four bone screw apertures 76 depicted in FIGS. 12-15, without changing the cage 12.

Turning now to FIGS. 20-23, the cover plate 16 and plate screw 18 will now be described in greater detail. The cover plate 16 helps retain bone screws 20 used in conjunction with the cage 12 and helps prevent the bone screws 20 from backing out with respect to the cage 12. Polyether ether ketone (PEEK) is a thermoplastic polymer that has been widely accepted for use in the manufacture of medical implants. PEEK has excellent mechanical, chemical resistance and biocompatible properties and has been finding increased use in spinal fusion devices as it mimics the stiffness of real bone. While many medical implants are made entirely of PEEK, many implants have both PEEK components and non-PEEK components such as stainless steel and titanium. The cover plate 16 may be made of PEEK or of metal such as surgical stainless steel and titanium or other appropriately suitable and biocompatible material.

Still referencing FIGS. 20-23, the cover plate 16 includes an inner surface 90 and an outer surface 92 interconnected by a top end 94, bottom end 96 and a first side 98 and second side 100. The cover plate 16 is configured for attachment to the screw plate 14 and, in particular, for attachment to the anterior surface 30 of the screw plate 14. The cover plate 16 has a curved contour that matches the curvature of the outer surface 66 of the screw plate 14 and is sized and configured to fit within the cover plate recess 78 such that the outer surface 92 is substantially flush with the outer surface 66 of the screw plate 14. The cover plate 16 includes a threaded plate screw aperture 102 configured to receive a plate screw 18 to attach the cover plate 16 to the screw plate 14. The cover plate 16 also includes two instrument apertures 104 configured for connection with an instrument used to carry the cover plate 16 to the surgical site and attach the cover plate 16 to the screw plate 14. The plate screw aperture 102 is located along the midline and the instrument apertures 104 are located on either side of the midline and the plate screw aperture 102. The cover plate 16 includes a wing 106 at each of the first side 98 and the second side 100. The wings 106 are sized and configured to fit inside the bone screw openings 76 on the screw plate 14. The wings 106 advantageously fill any extra space between the screw head 118 and the cover plate 14. As a void filler, the wings 106 advantageously provide better back-out protection for the bone screws 20 as there is less distance between the bone screw 20 and the screw plate 14. With the cover plate 16 in position and attached to the screw plate 14, the cover plate 16 covers at least partially the bone screw openings 76 and/or cover at least partially the bone screws 20 located in the bone screw openings 76 to prevent the bone screws 20 from backing out with respect to the cage 12 and/or screw plate 14. The cover plate 16 is typically made of biocompatible metal such as stainless, surgical steel, titanium and the like. The cover plate 16 may also be made of any other suitable material including but not limited to PEEK.

With particular reference to FIG. 22, the plate screw 18 will now be described in greater detail. The plate screw 18 includes a head 110 interconnected to a threaded shank 112. The head 110 has a lateral dimension that is larger than the lateral dimension of the shank 112. At the proximal end of the head 110, a longitudinal socket 116 is formed and configured to engage with a driving tool to rotate the plate screw 18 relative to the cover plate 16. A substantially hexagonal, daisy-shaped socket 116 is shown in FIG. 22; however, the socket 116 can be of any shape that allows an instrument to rotate the plate screw 18. The shank 112 is sized and configured to be inserted into the plate screw aperture 102 in the cover plate 16 and to thread into the plate screw aperture 74 in the screw plate 16 until the head 110 abuts the cover plate 16 and is substantially flush with the outer surface 92 of the cover plate 16.

Turning to FIG. 24, the bone screw 20 will be now described in greater detail. The bone screw 20 is an exemplary orthopedic fastener that is preferably used with the interbody spacer 10 of the present invention although other types of fasteners may be employed. The bone screw 20 includes a screw head 118, neck 120 and threaded shank 122. The head 118 is has a larger lateral dimension than the threaded shank 122. The outer surface of the head 118 may be curved, angled or spherical in shape or partially spherical or a frustum or frusta of a sphere having a region of a sphere delimited by one plane parallel to a plane containing a diameter or having a region of a sphere delimited by two planes which in one variation may be parallel to each other to mate with the bone screw apertures in order to provide for a smooth polyaxial angulation. The proximal end of the head 118 includes an opening that serves as an instrument recess or socket 124 configured to engage a complementary tip of a surgical tool for driving the bone screw into bone. A substantially hexagonal, daisy-shaped recess 124 is shown in FIG. 24; however, the recess 124 can be of any shape that allows a surgical tool to drive the bone screws 20 into the vertebral column. The head 118 of the bone screw 20 corresponds to the shape of the bone screw openings 76 in the screw plate 14. The bone screws 20 are configured to allow polyaxial, variable angle or fixed angled orientation with respect to the cage 12 while disposed inside the bone screw openings 76. The angulation of the bone screws 20 with respect to the cage 12 allows a desired angle or orientation with respect to the cage 12 and adjacent vertebral bodies to be achieved to anchor the cage 12 to the vertebrae. The bone screws 20 are preferably self-tapping and configured for insertion into bony material, however, other screws requiring holes to be drilled or pre-tapped can also be employed.

In use, the present interbody spacer 10 is configured for use as an ALIF cage in spinal surgical procedures. It is understood that novel features of the present invention can find application in different types of cages including but not limited to interbody spacers for PLIF, TLIF, XLIF surgical procedures as well as other types of orthopedic implants. Implanting the interbody spacer 10 involves removal, in whole or in part, of the disc material from the intervertebral space at the target vertebral level where the interbody spacer 10 will be implanted. The patient is oriented to provide some distraction of the disc space and to provide access to the anterior of the spine. Additional distraction of the disc space and surrounding tissues may be needed to decompress the nerve roots, realign the anatomical axis of the spine, and restore disc space height at the particular target level. After disc material is removed, a clean space is achieved in which to place the device. The vertebral endplates may be further prepared using burrs, curettes and the like to abrade and clean the endplates to encourage bone regeneration. A surgeon will then select an appropriately sized cage 12 that has the best size in footprint and height and lordotic angle for the target space. The surgeon may use an insertion instrument to grasp the cage 12 and place it at the mouth of the intervertebral space and move and orientate the cage 12 with or without the screw plate 14 attached into its proper orientation within the intervertebral space. The insertion instrument typically has two distal prongs configured to securely attach to the cage 12 at the instrument notches 42. The surgeon may determine the position of the cage 12 with the help of one or more x-ray fluoroshots. Since the position of the radiographic markers 22 are known relative to the cage 12, a surgeon can determine the position of the cage 12 in the target space by viewing the positions of the radiographic markers 22 embedded inside the radiographic pin holes 52 that appear in the x-ray and reposition the cage 12 as needed until final placement is achieved. The cage 12 may include bone graft or other material located inside the central opening(s) 44 of the cage 12 to promote ingrowth and blood supply in order to grow active and live bone from the adjacent spinal vertebrae to inter-knit with the spacer 10 and, thereby, eventually immobilize and fuse the adjunct spinal vertebrae. The cage 12 is placed such that the anterior surface 30 of the cage 12 faces the anterior side of the patient and the top surface 24 contacts the lower endplate of the upper vertebral body and the bottom surface 26 of the cage 12 contacts the upper endplate of the lower vertebral body on either side of the target intervertebral space. The geometry of the ridges 48 on the top surface 24 and the bottom surface 26 provide resistance to migration of the cage 12 while inside the target space. Other coatings and surface textures may also be provided on the cage 12. The surgeon may preassemble the screw plate 14 to the cage 12 prior to insertion into the vertebral space or the surgeon may insert the cage 12 first and then attach the screw plate 14 in situ. If the surgeon has not already attached the screw plate 14 to the cage 12, the surgeon will not push the cage 12 all the way into the vertebral space in order to allow for the attachment of the screw plate 14 to the cage 12 and rotation of the screw plate 14 with respect to cage 12 after which the cage 12 and screw plate 14 together are fully positioned within the vertebral space. The surgeon may determine how many bone screws 20 will be needed based on patient anatomy. The appropriate screw plate 14 containing three or four bone screw openings 76 is selected and attached to the cage 12 as previously described by orienting the screw plate 90 degrees with respect to the cage 12 and then rotating the screw plate 14 relative to the cage 12 to mate the tongue and grooves and engage the locking mechanism in order to secure the screw plate 14 to the cage 12. Next, bone screws 20 are deployed via a surgical instrument such as a bone screw driver. The bone screws 20 are inserted into the bone screw openings 76 and tapped into the bone of the adjoining vertebral bodies. The one or more bone screws 20 are passed through the cage 12 via the bone screw apertures 76 in a trajectory transverse to the longitudinal axis and into the upper and lower vertebral bones. As the bone screws 20 are tightened, the vertebral bodies penetrated with the bone screws 20 will compress onto both sides of the load-bearing cage 12 and provide pressure to help facilitate fusion. Additional bone graft material may be placed in the intervertebral disc space. An insertion instrument is provided that includes an elongate shaft having two pins at the its distal end. The pins are sized and configured for insertion through the instrument apertures 104 on the cover plate 16. The plate screw 18 is partially inserted into the plate screw aperture 102 and the cover plate 16 is mounted onto the pins 128 of the insertion instrument 126. The cover plate 16 and plate screw 18 are delivered to the outer surface 66 of the screw plate 14 and the protruding instrument pins are aligned placing the plate screw aperture 74 into alignment with the plate screw 18. The plate screw 18 is threadingly engaged with the threaded plate screw aperture 74 on the screw plate 14 and threaded with a driver. As the plate screw 18 is driven, the cover plate 16 and the wings 106 are drawn into the cover plate recess 76 and into the bone screw openings 76. With the plate screw 18 in place, the cover plate 16 resides inside the cover plate recess 78. The cover plate 16 is disposed over a head 118 of at least one of the plurality of bone screws 20 implanted together with the cage 12. The cover plate 16 is held in place over one of the plurality of bone screws 20 using a metallic plate screw 18 securely threaded into the plate screw aperture 74. The cover plate 16 serves as a locking plate and provides anti-back-out protection for the bone screws 12. When actuated, the plate screw 18 compresses the cover plate 16 against the body structure of the screw plate 14 which is in turn connected to the cage 12. The cover plate 16 locks the bone screws 20 into the cage and vertebral bodies and prevents them from loosening and backing out. In FIGS. 1-3 and 25-26 the bone screws 20 are shown at a given angle although any suitable angle(s) for a given application may be utilized and as may any suitable number of screws. Additional instrumentation such as rods or screws may also be used to further stabilize the spine across the target level. Any of the components in the present invention are manufactured from metal such as titanium, ceramic, plastic such as PEEK and carbon fiber reinforced polymer, biomaterial including but not limited to any of a number of biocompatible implantable polymers including PEKK, PEKEK, polyetheretherketone (PEEK) being preferred, titanium ceramic, bone or other material etc. The present invention can be employed and is suitable for use where ever the backing out of screws is to be prevented and anywhere along the spine including but not limited to cervical, thoracic, lumbar or sacral or between other bony structures outside of the spinal region. Embodiments of the present invention are standalone interbody devices which may be designed in the general style of an ALIF device, TLIF device, PLIF device or other device. In addition, the size and/or shape of the basic embodiments disclosed herein may be adapted by one skilled in the art for use in various levels of the spine, namely the cervical spine, thoracic spine and the lumbar spine. Thus, while various embodiments herein may be described by way of example with respect to the lumbar spine such disclosures apply with equal weight to the other levels of the spine.

Turning now to FIGS. 27-44, another variation of an interbody spacer 10 will now be described wherein like reference numbers are used to describe like parts. With reference first to FIGS. 27-30, an interbody spacer 10 according to one variation of the invention may be used to stabilize or fuse vertebral bodies in the lumbar or other region of the spine. The interbody spacer 10 comprises a cage 12, a screw plate 14, a retaining ring 19, and bone screws 20. The screw plate 14 is connected to the cage 12 to receive the bone screws 20 secured to the screw plate 14 via retaining rings 19 in order to retain the bone screws 20 disposed in the screw plate 14 and thereby connected to the cage 12. The bone screws 20 are configured relative to the cage to anchor the interbody spacer 10 between two bony components of the spine. Optional radiographic markers are embedding within the cage 12.

The cage 12 is the same cage 12 as described above with respect to FIGS. 4-7 and the description will not be repeated herein. Advantageously, the same cage 12 can be used interchangeably with any of the screw plates 14 described in this specification.

Turning now to FIGS. 31-34, the screw plate 14 will now be described in greater detail. The screw plate 14 serves as an interface for receiving the retaining ring 19 and bone screws 20. The screw plate 14 includes an inner surface 64 and an outer surface 66 interconnected by a top end 68, bottom end 70 and sides 72. The screw plate 14 is configured for attachment to the cage 12 and, in particular, for attachment to the anterior surface 30 of the cage 12. The screw plate 14 has a curved contour that matches the curvature of the cage sidewall 28 and is sized and configured to fit within the screw plate recess 38 such that the outer surface 66 is flush with the outer surface of the cage 12. The screw plate 14 includes one or more bone screw openings 76 sized and configured to receive bone screws 20 in a manner that permits their polyaxial angulation with respect to the screw plate 14 and cage 12. With the screw plate 14 in position and attached to the cage 12, the bone screw openings 76 are substantially aligned with the bone screw apertures 54 formed in the cage 12. One or more bone screw openings 76 are angled toward the top surface 24 such that bone screws 20 inserted therein are directed into the lower endplate of the adjacent upper vertebra. Two bone screw openings 76 are shown angled upwardly toward the upper vertebral body in the variation of FIGS. 27-34. One or more bone screw openings 76 are angled toward the bottom surface 26 such that bone screws 20 inserted therein are directed into the upper endplate of the adjacent lower vertebra. One bone screw opening 76 is shown angled downwardly toward the lower vertebral body in the variation of FIGS. 27-34. The bone screw opening 76 that is angled downwardly is formed between the two bone screw openings 76 that are angled upwardly and substantially along the midline of the cage 12. In the variation shown in FIGS. 35-38 and 42-43, two bone screw openings 76 are shown angled upwardly toward the upper vertebral body and two bone screw openings 76 are shown angled downwardly toward the lower vertebral body. Each bone screw opening 76 includes an interior ledge for contact with the head of the bone screw 20. The interior ledge divides the bone screw opening 76 into a bone screw shaft receiving portion and a bone screw head receiving portion. The inner diameter of the head receiving portion is larger than the inner diameter of the shaft receiving portion to accommodate the relatively larger head of the bone screw 20 and to permit it to angulate substantially polyaxially. The bone screw openings 76 are fluted to accommodate the polyaxial range of angulation of the bone screw 20 with respect to the cage 12. Each bone screw opening 76 includes a retaining ring receiving location 81 particularly visible in FIGS. 29-30. The retaining ring receiving location is a circumferential groove formed on the inside of each bone screw opening 76 that is sized and configured to receive a retaining ring 19. The retaining ring 19 is typically a C-shaped ring 19 that can be compressed in spring-like fashion to be inserted into the retaining ring receiving location 81 to create a larger ledge that mates with a corresponding groove on the bone screw 20 in a snap-fit engagement that prevents the bone screw 20 from backing out with respect to the screw plate 14 and cage 12.

Each of the sides 72 of screw plate 14 includes a tongue 80 near the inner surface 64 and a groove 82 sized and configured to mate with the groove 49 on the cage 12. The inner surface 64 of the screw plate 14 includes a post 84 extending outwardly from a recess 85 that is recessed with respect to the inner surface 64. The post 84 is sized and configured to fit inside the inner opening 34 in the protrusion 40 of the cage 12. The post 84 is substantially cylindrical in shape and includes at least a first scallop 86 at the bottom to accommodate a bone screw 20. A second scallop may or may not be formed at the bottom to accommodate a bone screw 20 if needed. Also, in the variation of FIGS. 35-38, there is no scallop 86. The outer surface of the post 84 includes a bump 88 to serve as a locking mechanism when engaged with the notch 23 inside the protrusion 40 of the cage 12. The edges of the recess 85 are curved and sized and configured to receive the protrusion 40 of the cage 12. The edges of the recess 85 also include a groove 89 best seen in FIG. 32. The groove 89 is sized and configured to receive the tongue 36 on the protrusion 40 of the cage 12. The configuration is generally a tongue 36 and groove on the protrusion 40 that is configured to mate with the complimentary tongue and groove 89 on the inside edges of the recess 85 of the screw plate 14. The screw plate 14 further includes a protuberance 83 extending outwardly from the inner surface 64 of the screw plate 14. The protuberance 83 is substantially cylindrical and sized and configured to fit inside and abut the stop 47 on the cage 12. The screw plate 14 is typically made of biocompatible metal such as polyether ether ketone (PEEK), stainless, surgical steel, titanium and any other suitable material. As shown in FIGS. 31-34, the screw plate 14 is designed with three bone screw openings 76 to receive three bone screws 20 for anchoring the cage 12 into adjacent vertebrae. An alternative variation is shown in FIGS. 35-38 where like reference numbers are used to describe like parts. The screw plate 14 of FIGS. 35-38 is includes four bone screw openings 76 in order to receive four bone screws 20 for anchoring the cage 12 into adjacent vertebrae. The screw plate 14 of FIGS. 31-34 and the screw plate of FIGS. 35-38 are advantageously interchangeable with the same cage 12 of FIGS. 4-7 as well as with the screw plate 14 of FIGS. 8-11 and FIGS. 12-15. It is up to surgeon preference which screw plate 14 to employ for a given anatomy. The surgeon is provided with both a three-bone-screw screw plate and a four-bone-screw screw plate, both of which can be advantageously mounted on the same cage 12 that the surgeon is using without having to remove the cage 12 or have a second cage 12 on hand that will accommodate more or fewer bone screws. Hence, the surgeon can decide during surgery how many bone screws 20 are necessary for a given anatomy given the uniqueness of each vertebrae and varying fragility of the bone from patient to patient. The surgeon simply choses the appropriate screw plate 14 either for accommodating three or four bone screws 20 and proceeds to mount the desired screw plate 14 on the cage 12. The cage 12 functions as a universal cage having bone screw apertures 54, ramped features or other cutouts in the design of the cage 12 that makes it configured to receive a variety of different screw plates 14. Advantageously, if the surgeon decides to implant a different number of bone screws 20, the screw plate 14 is easily removed and another screw plate with more or fewer bone screw openings 76 is mounted onto the cage 12. The mounting of the screw plate 14 onto the cage 12 will be described in greater detail below.

Turning now to FIGS. 39-40, the mounting of the screw plate 14 onto the cage 12 will now be described. The screw plate 14 is oriented at approximately 90 degrees with respect to the cage 12 as shown in FIG. 39. The post 84 on the screw plate 14 is inserted into the inner opening 34 on the cage 12. The tongue 80 and groove 82 on the sides 72 as well as the groove 89 at the edge of the recess 85 are clear from correspondingly mating groove 49 and tongue 36 on the cage 12 when the screw plate 14 is oriented in the 90-degree position. The screw plate 14 is then rotated with respect to the cage 12 by approximately 90 degrees in a clockwise direction as viewed from the anterior direction toward the outer surface 66 of the screw plate 14. As the screw plate 14 is rotated, the tongue 80 on the sides of the screw plate 14 will slide into the groove 49 on the cage 12 and with the rotation, the tongue 36 on the cage 12 will slide into groove 89 on the screw plate 14. Directional indicators such as arrows may be provided on the outer surface 66 of the screw plate 14 to provide an indication to user which side of the screw plate 14 should face up. With the help of the directional indicators, the user then rotates the screw plate 14 with respect to the cage 12 in the proper clockwise direction into a position shown in FIG. 40. The rotation is stopped by the protuberance 83 on the screw plate 14 coming into contact and abutting the stop 47 formed on the cage 12. Also, the bump 88 on the post 84 will snap into the notch 23 on the inner surface of the protrusion 40 to serve as a locking mechanism that prevents the rotation of the screw plate 14 with respect to the cage 12. The bump 88 and notch 23 interface prevents the counter-clockwise rotation of the screw plate 14 and the mating of the tongues and grooves prevent the screw plate 14 from detaching away from the cage 12. These two mechanisms advantageously secure the screw plate 14 to the cage 12. If the user wishes to remove the screw plate 14 from the cage 12, the user would rotate the screw plate 14 in a counter-clockwise direction with sufficient force to overcome the engagement of the notch 23 and bump 88 and further by approximately 90 degrees to disengage the mating of the tongues and grooves on the plate and cage. With the screw plate 14 removed, the user may advantageously substitute the removed screw plate 14 with another screw plate 14, such as the one having four bone screw apertures 76 depicted in FIGS. 35-38, without changing or removing the cage 12 from the anatomy.

Figure 29:
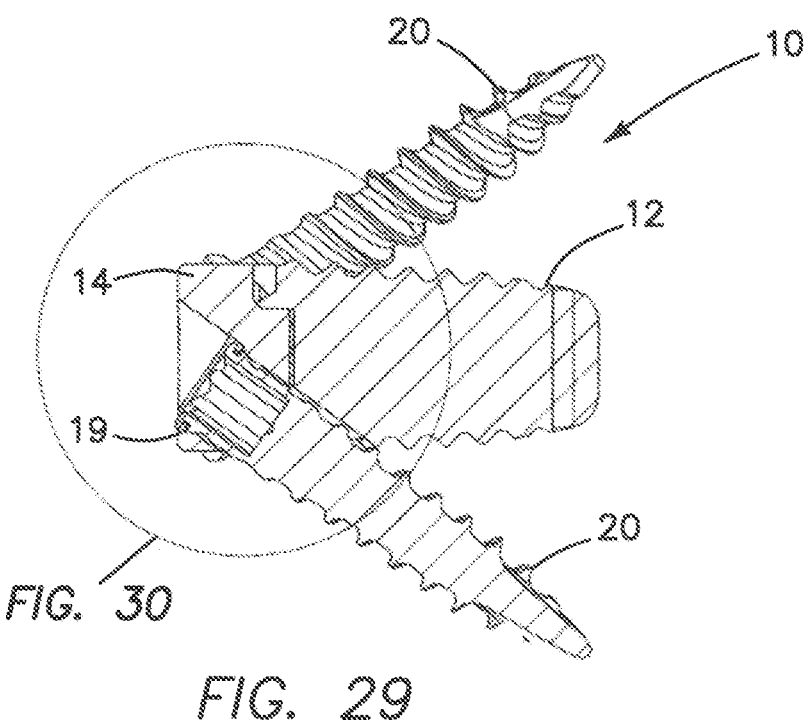
FIG. 29 is a cross-sectional view taken along line 29-29 of FIG. 28 of an interbody spacer according to the present invention.
Figure 30:
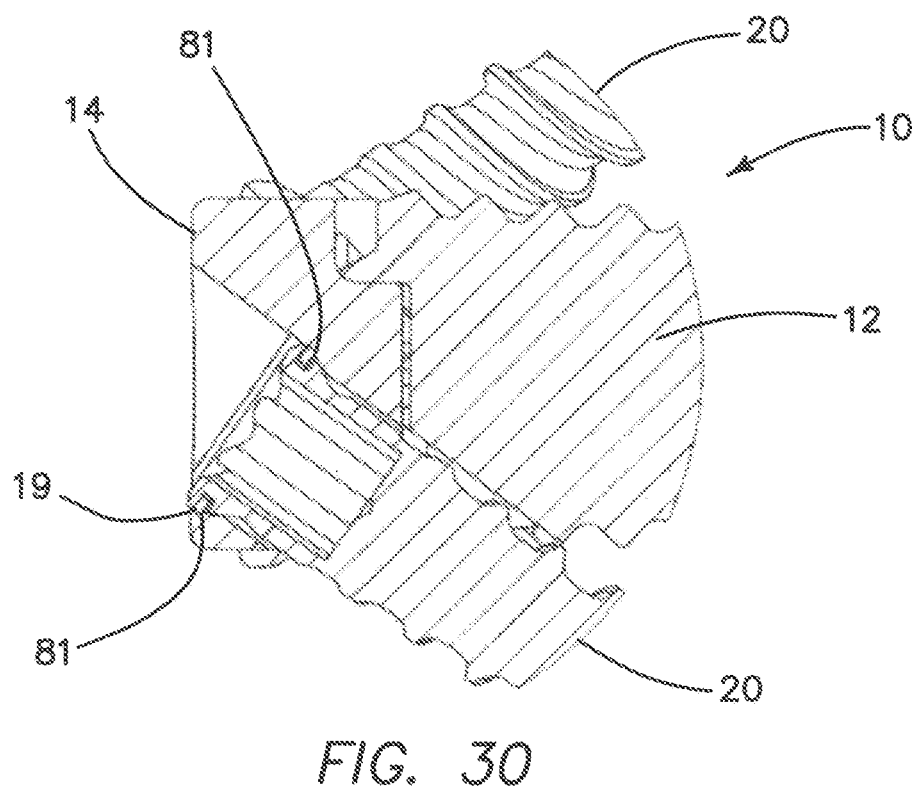
FIG. 30 is a detail view 30 of FIG. 29 an interbody spacer according to the present invention.
Figure 42:
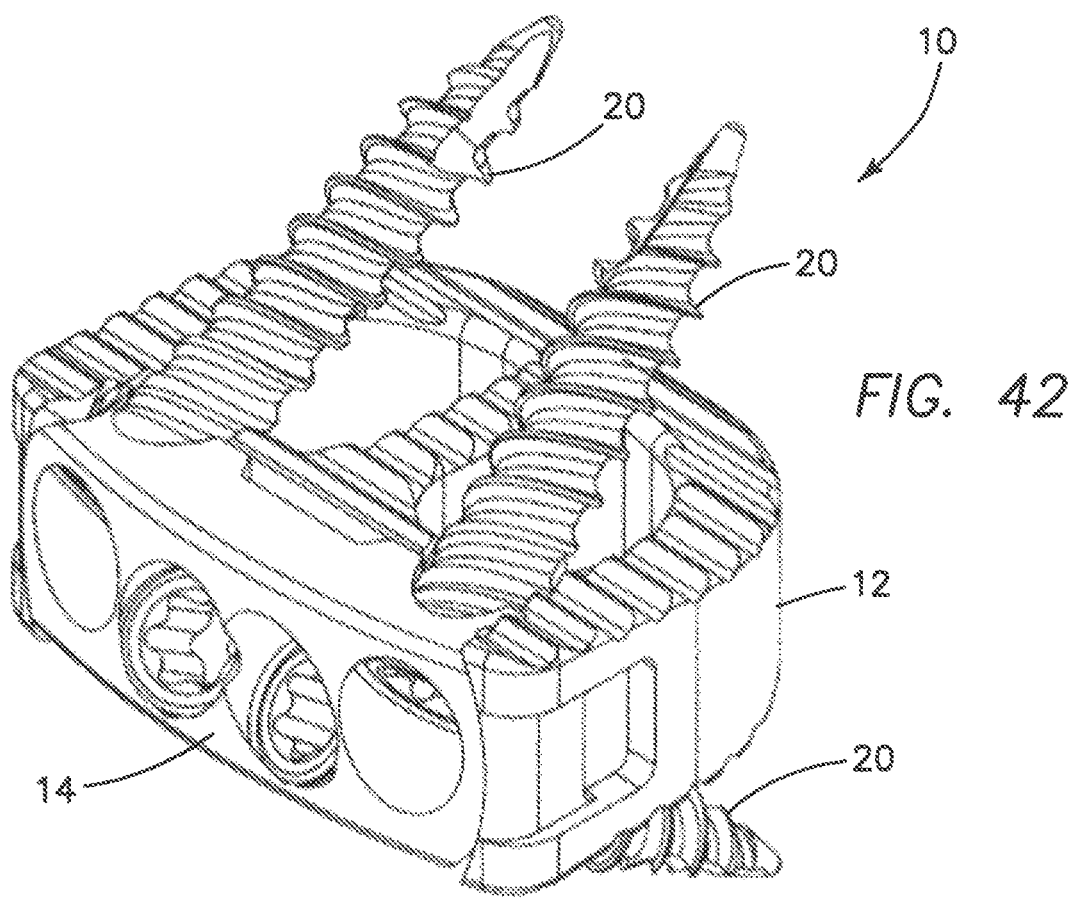
FIG. 42 is a top perspective view of an interbody spacer according to the present invention.
Figure 43:
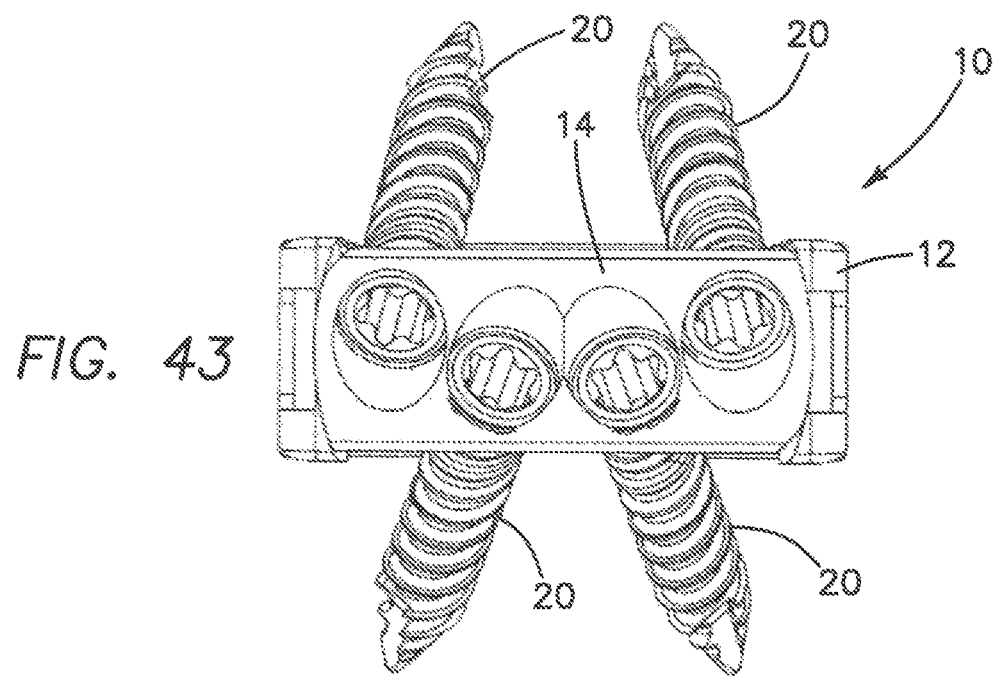
FIG. 43 is a front elevational view of an interbody spacer according to the present invention.
Figure 44:
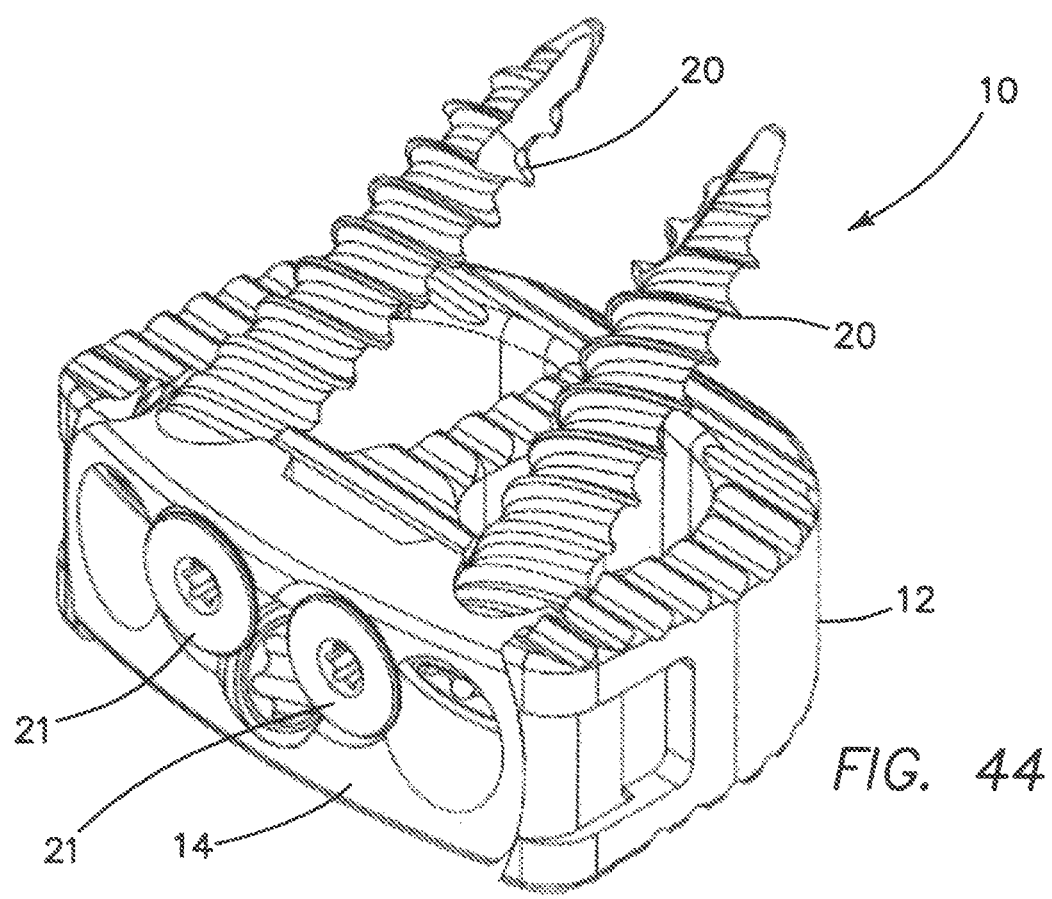
FIG. 44 is a top perspective view of an interbody spacer according to the present invention.
Figure 45:
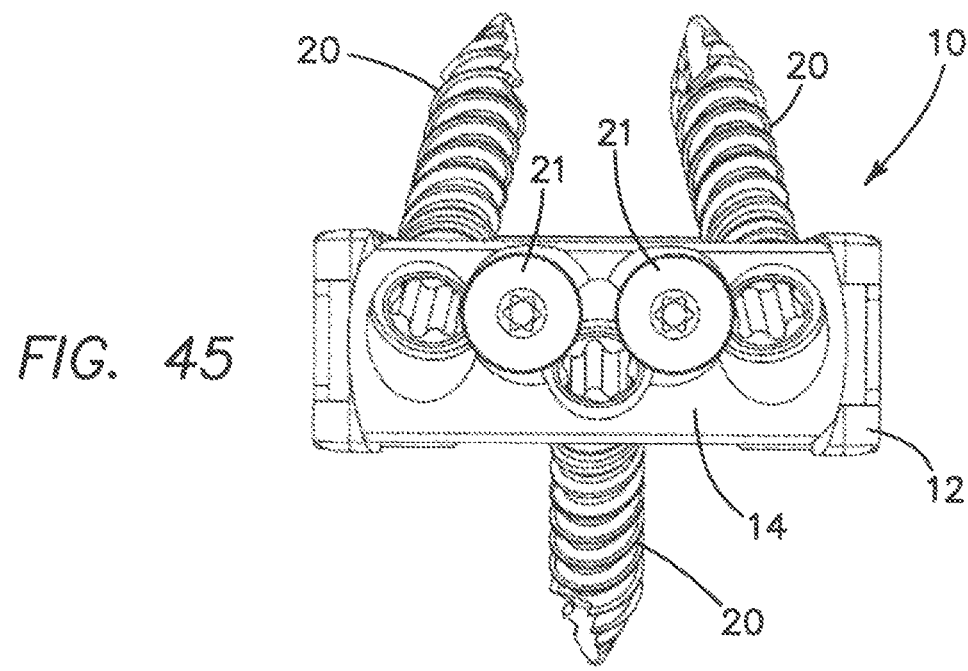
FIG. 45 is a front elevational view of an interbody spacer according to the present invention.
Figure 46:
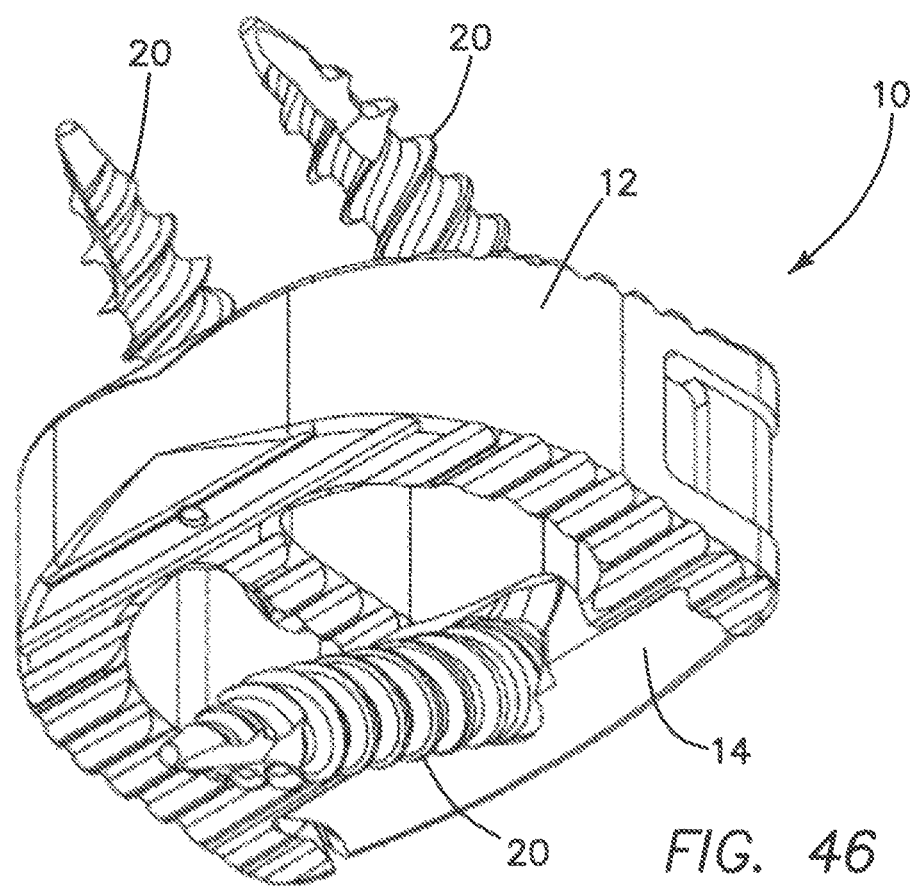
FIG. 46 is a rear, bottom perspective view of an interbody spacer according to the present invention.

With particular reference to FIG. 41, the retaining ring 19 will now be described in greater detail. The retaining ring 19 is a resilient C-shaped ring that can be compressed to a smaller diameter and spring back to its larger diameter shape and to thereby function as a spring. The retaining ring 19 is sized and configured to fit inside the retaining ring receiving location 81 formed on the inside of each bone screw opening 76 as shown in FIG. 29-30. To insert the retaining ring 19 into the retaining ring receiving location 81, the retaining ring 19 is slightly compressed and allowed to snap out into the retaining ring receiving location 81 on the cage 12. The retaining ring 19 remains seated and connected to the cage 12. The bone screw 20 is the same bone screw 20 as the bone screw 20 described above with respect to FIG. 24.

In use, the present interbody spacer 10 of FIGS. 27-43 is configured for use in the same manner as described with respect to the interbody spacer 10 of FIGS. 1-26. The interbody spacer 10 is pre-assembled by snapping the retaining ring 19 into the retaining ring 81 receiving location on the screw plate 14. The appropriate screw plate 14 for three bone screws 20 or screw plate 14 for four bone screw 20 is selected by the surgeon and is attached to the cage 12 by orienting the screw plate 14 approximately 90 degrees perpendicular to the cage 12 as shown in FIG. 39 and then rotating it into a horizontal position flush with cage 12 as shown in FIG. 40. The screw plate 14 may be preassembly or, alternatively, the screw plate 14 can be attached to the cage 12 in situ by inserting the cage 12 by itself at least partially into the vertebral space to permit room for attachment and rotation of the screw plate 14 with respect to the cage 12 after the surgeon selects the appropriate screw plate 14 (3 or 4 bone screw variation). After the selected screw plate 14 is attached to the cage 12 and the cage 12 and screw plate 14 combination is positioned within the vertebral space, the bone screws 20 are inserted into the bone screw openings 76 and into the vertebrae. The ramped or tapered neck 120 of the bone screw 20 helps the larger head 118 to move past the retaining ring 19. The surgeon will feel a tactile sensation when the bone screw 20 clicks past the retaining ring 19 indicating to the surgeon that the bone screw 20 is retained. The retaining ring 19 advantageously serves as back-out protection preventing the bone screw 20 from moving back out or loosening with respect to the screw plate 14 and cage 12 combination.

Turning now to FIGS. 44-62, another variation of an interbody spacer 10 will now be described wherein like reference numbers are used to describe like parts. With reference first to FIGS. 44-46 and 61-62, an interbody spacer 10 according to one variation of the invention may be used to stabilize or fuse vertebral bodies in the lumbar or other region of the spine. The interbody spacer 10 comprises a cage 12, a screw plate 14, at least one locking screw 21, and bone screws 20. The screw plate 14 is connected to the cage 12 to receive the bone screws 20 secured to the screw plate 14 via the locking screw 21 in order to retain the bone screws 20 disposed in the screw plate 14 and prevent the bone screws 20 from backing out. The bone screws 20 are configured relative to the cage to anchor the interbody spacer 10 between two bony components of the spine. Optional radiographic markers are embedding within the cage 12.

The cage 12 is the same cage 12 as described above with respect to FIGS. 4-7 and the description will not be repeated herein. Advantageously, the same cage 12 can be used interchangeably with any of the screw plates 14 described in this specification.

Turning now to FIGS. 47-50, the screw plate 14 will now be described in greater detail. The screw plate 14 serves as an interface for receiving the bone screws 20 and connecting them to the cage 12. Also, the screw plate 14 serves to receive and connect the locking screws 21 to the screw plate 14 and cage 12. The screw plate 14 includes an inner surface 64 and an outer surface 66 interconnected by a top end 68, bottom end 70 and sides 72. The screw plate 14 is configured for attachment to the cage 12 and, in particular, for attachment to the anterior surface 30 of the cage 12. The screw plate 14 has a curved contour that matches the curvature of the cage sidewall 28 and is sized and configured to fit within the screw plate recess 38 such that the outer surface 66 is flush with the outer surface of the cage 12. The screw plate 14 includes at least one threaded locking screw aperture 74 configured to receive a locking screw 21 to cover one or more bone screws 20 inserted into the screw plate 14 and into cage 12. The locking screw aperture 130 extends from the outer surface 66 to the inner surface 64 of the screw plate 14. Each locking screw aperture 130 includes a circumferential recess also called an indentation that surrounds each locking screw aperture 130. The indentation serves to recess the head of the locking screw 21 so that it is substantially flush with the outer surface 66. The screw plate 14 includes one or more bone screw openings 76 sized and configured to receive bone screws 20 in a manner that permits their polyaxial angulation with respect to the screw plate 14 and cage 12. With the screw plate 14 in position and attached to the cage 12, the bone screw openings 76 are substantially aligned with the bone screw apertures 54 formed in the cage 12 or otherwise have clearance directly from the screw plate 14 into the vertebral body. One or more bone screw openings 76 are angled toward the top surface 24 such that bone screws 20 inserted therein are directed into the lower endplate of the adjacent upper vertebra. Two bone screw openings 76 are shown angled upwardly toward the upper vertebral body in the variation of FIGS. 44-50. One or more bone screw openings 76 are angled toward the bottom surface 26 such that bone screws 20 inserted therein are directed into the upper endplate of the adjacent lower vertebra. One bone screw opening 76 is shown angled downwardly toward the lower vertebral body in the variation of FIGS. 44-50. The bone screw opening 76 that is angled downwardly is formed between the two bone screw openings 76 that are angled upwardly and substantially along the midline of the cage 12. In the variation shown in FIGS. 53-56 and 61-62, two bone screw openings 76 are shown angled upwardly toward the upper vertebral body and two bone screw openings 76 are shown angled downwardly toward the lower vertebral body. Each bone screw opening 76 includes an interior ledge for contact with the head of the bone screw 20. The interior ledge divides the bone screw opening 76 into a bone screw shaft receiving portion and a bone screw head receiving portion. The inner diameter of the head receiving portion is larger than the inner diameter of the shaft receiving portion to accommodate the relatively larger head of the bone screw 20 and to permit it to angulate substantially polyaxially. The bone screw openings 76 are fluted to accommodate the polyaxial range of angulation of the bone screw 20 with respect to the cage 12. Each of the sides 72 of screw plate 14 includes a tongue 80 near the inner surface 64 and a groove 82 sized and configured to mate with the groove 49 on the cage 12. The inner surface 64 of the screw plate 14 includes a post 84 extending outwardly from a recess 85 with respect to the inner surface 64. The post 84 is sized and configured to fit inside the inner opening 34 in the protrusion 40 of the cage 12. The post 84 is substantially cylindrical in shape and includes at least a first scallop 86 to accommodate a bone screw 20. The outer surface of the post 84 includes a bump 88 to serve as a locking mechanism when engaged with the notch 23 inside the protrusion 40 of the cage 12. The bump 88 is best seen in FIGS. 49 and 55. The edges of the recess 85 are curved and sized and configured to receive the protrusion 40 of the cage 12. The edges of the recess 85 also include a groove 89 best seen in FIGS. 48 and 49. The groove 89 is sized and configured to receive the tongue 36 on the protrusion 40 of the cage 12. The configuration is generally a tongue 36 and groove on the protrusion 40 that is configured to mate with the tongue and groove 89 on the inside edges of the recess 85 of the screw plate 14. The screw plate 14 further includes a protuberance 83 extending outwardly from the inner surface 64 of the screw plate 14. The protuberance 83 is substantially cylindrical and sized and configured to fit inside and abut the stop 47 on the cage 12. The screw plate 14 is typically made of biocompatible metal such as polyether ether ketone (PEEK), stainless, surgical steel, titanium and any other suitable material. As shown in FIGS. 44-50, the screw plate 14 is designed with three bone screw openings 76 to receive three bone screws 20 for anchoring the cage 12 into adjacent vertebrae. An alternative variation is shown in FIGS. 53-56 and 59-60 where like reference numbers are used to describe like parts. The screw plate 14 of FIGS. 53-56 and 59-60 includes four bone screw openings 76 in order to receive four bone screws 20 for anchoring the cage 12 into adjacent vertebrae. The screw plate 14 of FIGS. 44-50 and the screw plate of FIGS. 53-56 are advantageously interchangeable with the same cage 12 of FIGS. 4-7. It is up to surgeon preference which screw plate 14 to employ for a given anatomy. The surgeon is provided with both a three-bone-screw screw plate and a four-bone-screw screw plate, both of which can be advantageously mounted on the same cage 12 that the surgeon is using without having to remove the cage 12 or have a second cage 12 on hand that will accommodate more or fewer bone screws. Hence, the surgeon can decide during surgery how many bone screws 20 are necessary for a given anatomy given the uniqueness of each vertebrae and varying fragility of the bone. The surgeon simply choses the appropriate screw plate 14 either for accommodating three or four bone screws 20 and proceeds to mount the desired screw plate 14 on the cage 12 in situ or prior to insertion between vertebrae. Advantageously, if the surgeon decides to implant a different number of bone screws 20, the screw plate 14 is easily removed and another screw plate 14 with more or fewer bone screw openings 76 is mounted onto the cage 12. The mounting of the screw plate 14 onto the cage 12 will be described in greater detail below.

Figure 59:
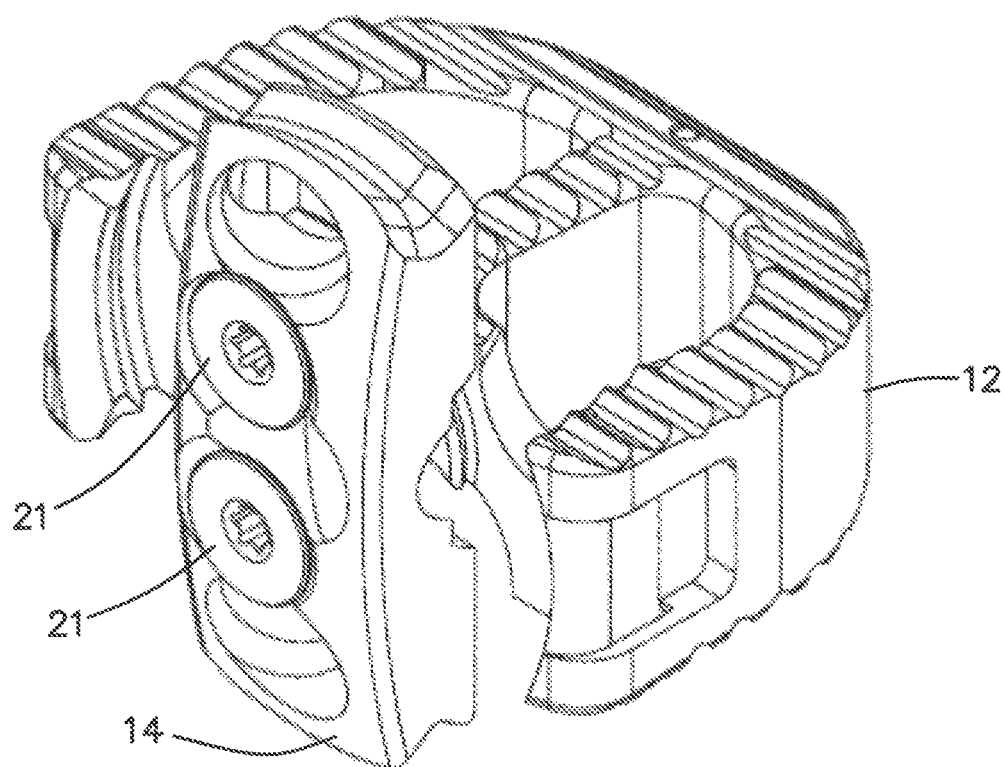
FIG. 59 is a top perspective view of a cage and a screw plate according to the present invention.
Figure 60:
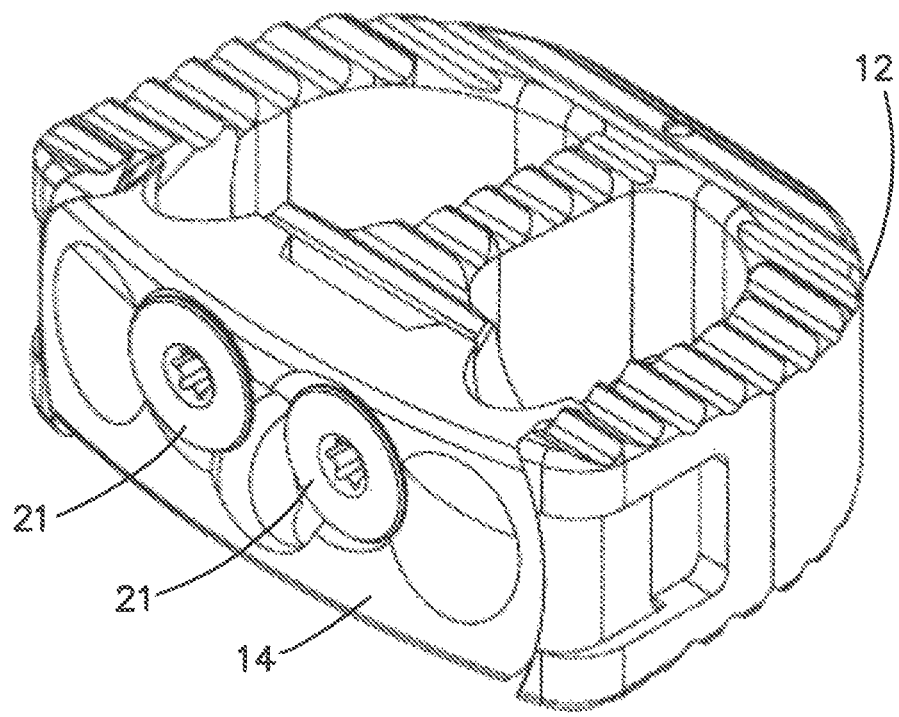
FIG. 60 is a top perspective view of cage and screw plate according to the present invention.
Figure 61:
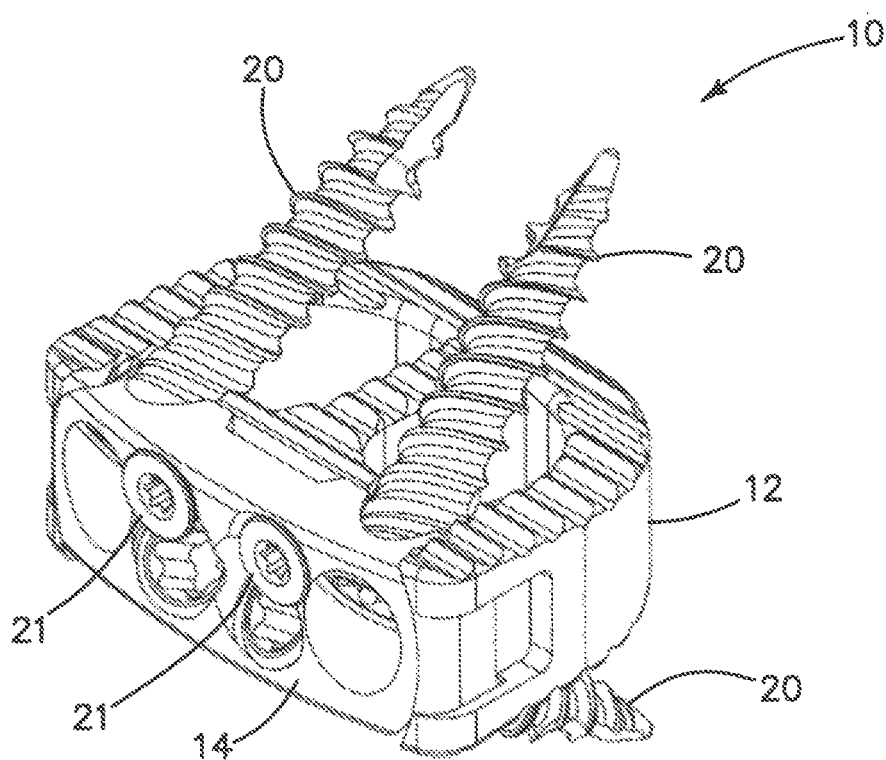
FIG. 61 is a top perspective view of an interbody spacer according to the present invention.
Figure 62:
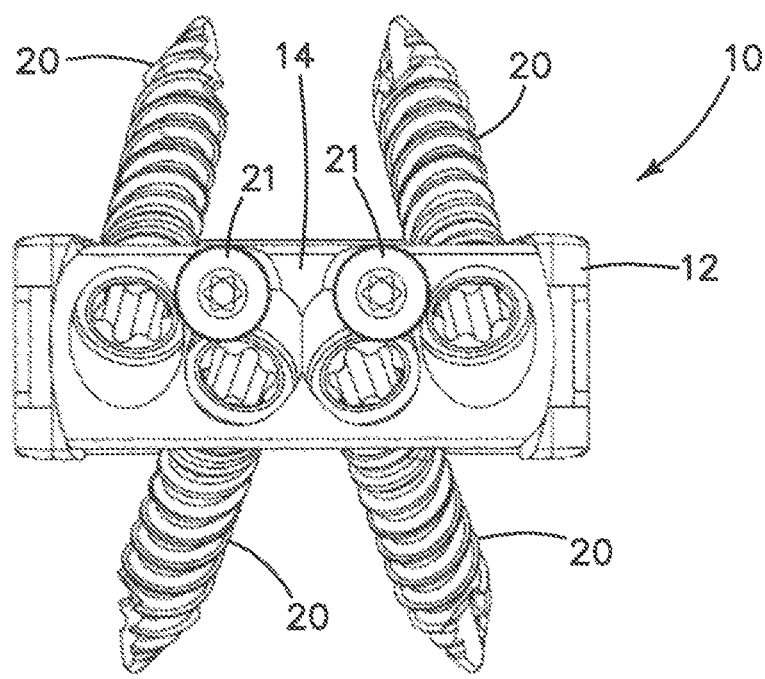
FIG. 62 is a front elevational view of an interbody spacer according to the present invention.

Turning now to FIGS. 59-60, the mounting of the screw plate 14 onto the cage 12 will now be described. The screw plate 14 is oriented at approximately 90 degrees with respect to the cage 12 as shown in FIG. 59. Locking screws 21 may be pre-inserted as shown. The post 84 on the screw plate 14 is inserted into the inner opening 34 on the cage 12. The tongue 80 and groove 82 on the sides 72 as well as the groove 89 at the edge of the recess 85 are clear from corresponding mating groove 49 and tongue 36 on the cage 12. The screw plate 14 is then rotated with respect to the cage 12 by approximately 90 degrees in a clockwise direction as viewed from the anterior direction toward the outer surface 66 of the screw plate 14. As the screw plate 14 is rotated, the tongue 80 on the sides of the screw plate 14 will slide into the groove 49 on the cage 12 and with the rotation, the tongue 36 on the cage 12 will slide into groove 89 on the screw plate 14. Directional indicators such as arrows may be provided on the outer surface 66 of the screw plate 14 to provide an indication to user a rotation direction or which side of the screw plate 14 should face up. With the help of the directional indicators, the user then rotates the screw plate 14 with respect to the cage 12 in the proper clockwise direction into a position shown in FIG. 60. The rotation is stopped by the protuberance 83 on the screw plate 14 coming into contact and abutting the stop 47 formed on the cage 12. Also, the bump 88 on the post 84 will snap into the notch 23 on the inner surface of the protrusion 40 to serve as a locking mechanism preventing the rotation of the screw plate 14 with respect to the cage 12. The bump 88 and notch 23 interface prevents further clockwise rotation and counter-clockwise rotation of the screw plate 14 and the mating of the tongues and grooves prevent the screw plate 14 from detaching away from the cage 12. These two mechanisms advantageously secure the screw plate 14 to the cage 12. If the user wishes to remove the screw plate 14 from the cage 12, the user would rotate the screw plate 14 in a counter-clockwise direction with sufficient force to overcome the engagement of the notch 23 and bump 88 and further by approximately 90 degrees to disengage the mating of the tongues and grooves. With the screw plate 14 removed, the user may advantageously substitute the removed screw plate 14 with another screw plate 14, such as the one having four bone screw apertures 76 depicted in FIGS. 53-56 or another screw plate 14 described in this specification, without changing the cage 12.

Figure 51:
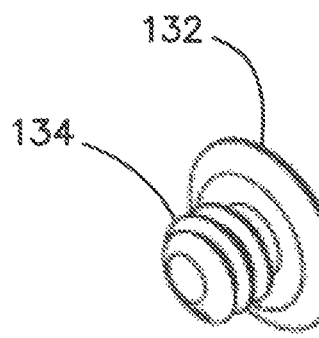
FIG. 51 is top perspective view of a locking screw according to the present invention.
Figure 57:
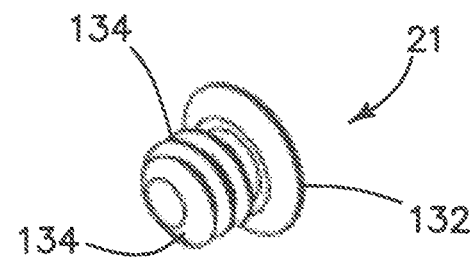
FIG. 57 is a top perspective view of a locking screw according to the present invention.
Figures 52, 58:
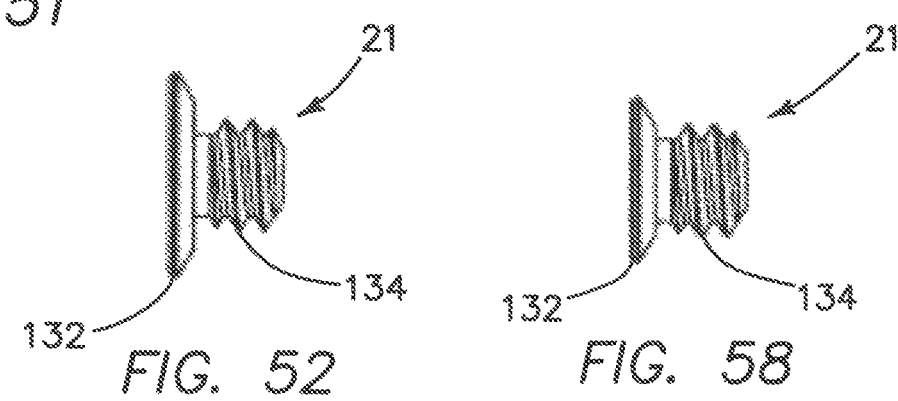
FIG. 52 is a side elevational view of a locking screw according to the present invention.
FIG. 58 is a side elevational view of a locking screw according to the present invention.

Turning now to FIGS. 51-52 and 57-58, the locking screw 21 will now be described in greater detail. The locking screws 21 retain bone screws 20 and prevents the bone screws 20 from backing out with respect to the cage 12. The locking screw 21 includes a head 132 interconnected to a threaded shank 134. The head 132 has a lateral dimension that is larger than the lateral dimension of the shank 112. At the proximal end of the head 132, a longitudinal socket is formed and configured to engage with a driving tool to rotate the locking screw 21 relative to the screw plate 14. The shank 134 is sized and configured to be inserted and threaded into the locking screw aperture 130 in the screw plate 14 until the head 132 abuts the screw plate 14 and is substantially flush with the outer surface 66 of the screw plate 14. The head 132 of the locking screw 21 for the three-bone screw plate pictured in FIGS. 51-52 is larger than the head 132 of the locking screw 21 for the four-bone screw plate of FIGS. 57-58. The head 132 protrudes radially outwardly like a circumferential flange to provide sufficiently cover the head 118 of the bone screw 20. Each locking screw 21 is located between two adjacent bone screw openings 76 and configured to cover two adjacent bone screws when inserted. For the 3-bone screw plate variation, the middle bone screw is advantageously covered by two locking screw 21. In the 4-bone screw plate variation, two bone screws are covered by one locking screw 21. The head 132 of the 3-bone screw plate variation is larger as there is more space on the cage 12 relative to the 4-bone screw plate variation. When the locking screw 21 is inserted into a locking screw aperture 130, at least part of the head 132 is positioned above and in intersection with the insertion and removal pathway of the bone screw 20 such that the flange-like head 132 prevents the bone screw 20 from backing out of the bone screw openings 76 and loosening with respect to the cage 12.

Turning to FIG. 24, the bone screw 20 will be now described in greater detail. The bone screw 20 is an exemplary orthopedic fastener that is preferably used with the interbody spacer 10 of the present invention although other types of fasteners may be employed. The bone screw 20 includes a screw head 118, neck 120 and threaded shank 122. The head 118 is has a larger lateral dimension than the threaded shank 122. The outer surface of the head 118 may be curved, angled or spherical in shape or partially spherical or a frustum or frusta of a sphere having a region of a sphere delimited by one plane parallel to a plane containing a diameter or having a region of a sphere delimited by two planes which in one variation may be parallel to each other to mate with the bone screw apertures in order to provide for a smooth polyaxial angulation. The proximal end of the head 118 includes an opening that serves as an instrument recess or socket 124 configured to engage a complementary tip of a surgical tool for driving the bone screw into bone. A substantially hexagonal, daisy-shaped recess 124 is shown in FIG. 24; however, the recess 124 can be of any shape that allows a surgical tool to drive the bone screws 20 into the vertebral column. The head 118 of the bone screw 20 corresponds to the shape of the bone screw openings 76 in the screw plate 14. The bone screws 20 are configured to allow polyaxial, variable angle or fixed angled orientation with respect to the cage 12 while disposed inside the bone screw openings 76. The angulation of the bone screws 20 with respect to the cage 12 allows a desired angle or orientation with respect to the cage 12 and adjacent vertebral bodies to be achieved to anchor the cage 12 to the vertebrae. The bone screw 20 used with the interbody spacer 10 of FIGS. 44-62 is the same bone screw 20 as the bone screw 20 described above with respect to FIG. 24.

In use, the interbody spacer 10 of FIGS. 44-62 is configured for use in the same manner as described with respect to the interbody spacers 10 of FIGS. 1-43. The interbody spacer 10 is pre-assembled by threading the locking screws 21 into the locking screw apertures 130. The locking screws 21 are not threaded all the way into the locking screw apertures 130 to leave enough space to permit passage of the bone screws 20 past the locking screw 21 and into the cage. Alternatively, the locking screws 21 may be left removed from the screw plate 14 and inserted after the cage 12 and screw plate 14 have been implanted into the vertebral space. The appropriate screw plate 14 for three bone screws 20 or screw plate 14 for four bone screw 20 is selected by the surgeon and is attached to the cage 12 by orienting the screw plate 14 approximately 90 degrees perpendicular to the cage 12 as shown in FIG. 59 and then rotating it into a horizontal position flush with cage 12 as shown in FIG. 60. The screw plate 14 may be preassembly, that is, the screw plate 14 may be attached to cage 12 or, alternatively, the screw plate 14 can be attached to the cage 12 in situ by inserting the cage 12 by itself at least partially into the vertebral space to permit room for attachment and rotation of the screw plate 14 with respect to the cage 12 after the surgeon selects the appropriate screw plate 14 (3 or 4 bone screw variation). In such a scenario, after the selected screw plate 14 is attached to the cage 12 and the cage 12 and screw plate 14 is fully moved into positioned within the vertebral space, the bone screws 20 are inserted into the bone screw openings 76 and into the vertebrae. With the bone screws 20 fully implanted, the locking screws 21 may be inserted or, if already preassembled, the locking screws 21 are threaded fully into the screw plate 14. The locking screws 21 are threaded into the screw plate 14 to cover and stand in the way of the insertion/removal pathway of the bone screw 20 and bear down onto the head 118 of the bone screw 20. The locking screw 21 and, in particular, the flange-like head 132 of the bone screw 20 advantageously serves as back-out protection preventing the bone screw 20 from moving back out or loosening with respect to the screw plate 14 and cage 12 combination.

It is understood that various modifications may be made to the embodiments of the interbody spacer disclosed herein. Therefore, the above description should not be construed as limiting, but merely as exemplifications of preferred embodiments. Those skilled in the art will envision other modifications within the scope and spirit of the present disclosure.

We claim:

1. An interbody spacer assembly for a spine, comprising:
a cage having at least four bone screw cutouts, and a top surface and a bottom surface interconnected by a sidewall, wherein the sidewall defines a front surface;
a first screw plate configured to be connected to the cage and having no more than three bone screw openings configured to be substantially aligned with three of the at least four bone screw cutouts of the cage;
a plurality of bone screws, wherein one bone screw is configured to be inserted into each bone screw opening of the first screw plate and each corresponding bone screw cutout of the cage; each bone screw having a head at a proximal end and a threaded shank extending toward a distal end for anchoring into bone; and each bone screw being configured to secure the cage between two bony components of a spine;
a cover plate sized and configured to be connected to the first screw plate and configured to prevent the bone screws from backing out relative to the first screw plate; and
wherein the first screw plate is interchangeable with a second screw plate, wherein both the first screw plate and the second screw plate are connectable to the cage separately, wherein a selected one of the first screw plate and the second screw plate is connected to the cage based on a surgeon's preference, the second screw plate having no more than four bone screw openings configured to be substantially aligned with four of the at least four bone screw cutouts of the cage for receiving four bone screws; and wherein the cover plate is further sized and configured to be connected to the second screw plate to prevent the bone screws from backing out relative to the second screw plate when the second screw plate is connected to the cage.

2. The interbody spacer assembly of claim 1 wherein the cover plate has a plate screw aperture configured to receive a plate screw for attaching the cover plate to the respective screw plate; the cover plate being removably connected to the cage with a plate screw inserted into the plate screw aperture; and the cover plate being configured to cover each bone screw head to prevent each bone screw from backing out.

3. The interbody spacer assembly of claim 2 wherein the sidewall of the cage defines a front surface and the front surface defines a recess sized and configured to receive the respective screw plate.

4. An interbody spacer assembly for a spine, comprising:
a cage having a longitudinal axis, at least two bone screw cutouts, and a top surface and a bottom surface interconnected by a sidewall, wherein the sidewall defines a front surface;
a screw plate connected to the cage and having an inner surface and an outer surface interconnected by a top end, a bottom end and two sides, and at least two bone screw openings substantially aligned with the at least two bone screw cutouts;
a plurality of bone screws, wherein one bone screw is inserted into each bone screw opening of the screw plate; each bone screw having a head at a proximal end and a threaded shank extending toward a distal end for anchoring into bone; each head having a larger diameter than the respective shank; and each bone screw being configured to secure the cage to a spine; and
a cover plate connected to the screw plate and configured to prevent the bone screws from backing out relative to the screw plate;
wherein the front surface of the cage includes a screw plate recess; wherein the screw plate recess has two sides oppositely disposed from each other defining the screw plate recess therebetween; wherein the two sides of the screw plate recess mate with the two sides of the screw plate via corresponding mating surfaces;
wherein the screw plate includes a post extending outwardly from the inner surface and the cage includes a protrusion extending outwardly from the front surface; the protrusion having an inner opening sized and configured to receive the post, and wherein the screw plate is sized and configured to rotate with respect to the cage into mating engagement with the two sides of the screw plate recess.

5. The interbody spacer assembly of claim 4 wherein the corresponding mating surfaces are tongue and groove surfaces.

6. The interbody spacer assembly of claim 4 wherein the protrusion defines two oppositely disposed sides and the post defines two oppositely disposed sides; wherein the two sides of the protrusion mate with the two sides of the post via correspondingly mating surfaces.

7. The interbody spacer assembly of claim 4 wherein the screw plate is rotatable with respect to the front surface of the cage between a substantially vertical orientation in which the two sides of the screw plate and the two sides of the recess are not engaged and a horizontal orientation in which the two sides of the screw plate and the two sides of the recess are engaged.

8. An interbody spacer assembly for a spine, comprising:
a cage having a longitudinal axis, at least two bone screw cutouts each sized and configured to receive a bone screw, a top surface and a bottom surface interconnected by a sidewall defining a front surface, a protrusion extending outwardly from a central portion of the front surface and having an inner opening defining an inner surface, and a notch formed in the inner surface;
a screw plate connected to the cage and having an inner surface and an outer surface interconnected by a top end, a bottom end and two sides, at least two bone screw openings substantially aligned with the at least two bone screw cutouts and each sized and configured to receive a bone screw, a post extending outwardly from a central portion of the inner surface of the screw plate and being sized and configured to be inserted into the inner opening of the protrusion, the post further including an outwardly extending bump sized and configured to lockingly mate with the notch, a protuberance extending outwardly from the inner surface of the screw plate and a stop formed on the front surface of the cage; wherein the protuberance is sized and configured to fit inside and abut the stop on the cage to prevent rotation of the screw plate relative to the cage when the screw plate is connected to the cage; and
a plurality of bone screws, wherein one bone screw is inserted into each bone screw opening of the screw plate and configured to secure the cage to a spine; each bone screw having a head at a proximal end and a threaded shank extending toward a distal end for anchoring into bone; each head having a larger diameter than the respective shank;
wherein the screw plate is attached to the front surface of the cage by rotating the screw plate with respect to the cage to bring the bump into engagement with the notch; and wherein mating of the bump and notch is configured to prevent rotation of the screw plate relative to the cage.

9. The interbody spacer assembly of claim 8 wherein the screw plate is configured to be connected in a front-loading fashion to the cage and rotated approximately 90 degrees into a locked position wherein the bump mates with the notch.

10. An interbody spacer assembly for a spine, comprising:
a cage having a longitudinal axis, at least two bone screw cutouts each sized and configured to receive a bone screw, a top surface and a bottom surface interconnected by a sidewall defining a front surface, a protrusion extending outwardly from the front surface and having an inner opening defining an inner surface; and a notch formed in the inner surface;
a screw plate connected to the cage and having an inner surface and an outer surface interconnected by a top end, a bottom end and two sides, at least two bone screw openings substantially aligned with the at least two bone screw cutouts and each sized and configured to receive a bone screw and a post extending outwardly from the inner surface and being sized and configured to be inserted into the inner opening of the protrusion; the post further including an outwardly extending bump sized and configured to mate with the notch;
and a plurality of bone screws, wherein one bone screw is inserted into each bone screw opening of the screw plate and configured to secure the cage to a spine; each bone screw having a head at a proximal end and a threaded shank extending toward a distal end for anchoring into bone; each head having a larger diameter than the respective shank;
wherein the screw plate is attached to the front surface of the cage by rotating the screw plate with respect to the cage to bring the bump into engagement with the notch; and wherein mating of the bump and notch is configured to prevent rotation of the screw plate relative to the cage; and
a protuberance extending outwardly from the inner surface of the screw plate and a stop formed on the front surface of the cage; wherein rotation of the screw plate relative to the cage brings the protuberance into abutment with the stop to prevent further rotation of the screw plate relative to the cage.

* * * * *